US010314955B2

(12) United States Patent
Friedman et al.

(10) Patent No.: US 10,314,955 B2
(45) Date of Patent: Jun. 11, 2019

(54) SYSTEMS AND METHODS FOR MEDICAL DEVICE CONTROL

(71) Applicant: LifeCell Corporation, Branchburg, NJ (US)

(72) Inventors: Evan Friedman, Montvale, NJ (US); Israel James Jessop, Annandale, NJ (US); Kai-Roy Wang, Jersey City, NJ (US); Aaron Barere, Hoboken, NJ (US); Brendan P. Collins, Manchester, NH (US); Derek Hugger, Goffstown, NH (US); Christopher Labak, Brookline, NH (US); Scott Woodruff, Chicago, IL (US)

(73) Assignee: LifeCell Corporation, Madison, NJ (US)

( * ) Notice: Subject to any disclaimer, the term of this patent is extended or adjusted under 35 U.S.C. 154(b) by 362 days.

(21) Appl. No.: 15/331,117

(22) Filed: Oct. 21, 2016

(65) Prior Publication Data

US 2017/0112981 A1 Apr. 27, 2017

Related U.S. Application Data

(60) Provisional application No. 62/381,116, filed on Aug. 30, 2016, provisional application No. 62/244,398, filed on Oct. 21, 2015.

(51) Int. Cl.
*A61M 1/00* (2006.01)
*C12M 1/33* (2006.01)
(Continued)

(52) U.S. Cl.
CPC ........ *A61M 1/0094* (2014.02); *A61M 1/0001* (2013.01); *A61M 1/0035* (2014.02);
(Continued)

(58) Field of Classification Search
CPC .............. A61M 1/0094; A61M 1/0035; A61M 1/0001; A61M 1/0058; A61M 39/223;
(Continued)

(56) References Cited

U.S. PATENT DOCUMENTS 3,791,524 A * 2/1974 Cho .................. A61B 10/0096
210/232
4,457,339 A 7/1984 Juan et al.
(Continued)

FOREIGN PATENT DOCUMENTS

EP 0512769 A2 11/1992
JP 2009189282 A 8/2009
(Continued)

OTHER PUBLICATIONS

International Search Report and Written Opinion for Application No. PCT/US2016/058171, dated Apr. 25, 2017. 14 pages.
(Continued)

*Primary Examiner* — Tatyana Zalukaeva
*Assistant Examiner* — Gabriella E Burnette
(74) *Attorney, Agent, or Firm* — McCarter & English, LLP; Matthew R. Van Eman

(57) ABSTRACT

Systems, devices, and methods of the present disclosure assist with management of tubes and hoses during surgical procedures. The systems, devices, and methods provide for the proper opening and closing of tubes to facilitate performance of steps in a surgical procedure. Systems, devices, and methods of the present disclosure control fluid delivery to and from a medical device, including devices for tissue processing and cleaning.

29 Claims, 24 Drawing Sheets

(51) Int. Cl.
*A61B 17/00* (2006.01)
*A61B 18/00* (2006.01)
*A61K 35/35* (2015.01)
*A61M 39/22* (2006.01)
*C12N 5/077* (2010.01)
*C12M 1/00* (2006.01)
*A61M 39/28* (2006.01)

(52) U.S. Cl.
CPC .......... *A61M 39/223* (2013.01); *A61M 39/28* (2013.01); *C12M 45/00* (2013.01); *C12N 5/0653* (2013.01); *A61B 2017/00792* (2013.01); *A61B 2018/00464* (2013.01); *A61K 35/35* (2013.01); *A61M 1/0058* (2013.01); *A61M 2202/08* (2013.01); *A61M 2205/3334* (2013.01); *A61M 2205/75* (2013.01); *C12M 45/02* (2013.01)

(58) Field of Classification Search
CPC .............. A61M 39/28; A61M 2202/08; A61M 2205/3334; A61M 2205/75; C12M 45/00; C12N 5/0653; A61B 2017/00792; A61B 2018/00464; A61K 35/35
See application file for complete search history.

(56) References Cited

U.S. PATENT DOCUMENTS

| | | | |
|---|---|---|---|
| 4,681,571 A | 7/1987 | Nehring | |
| 4,753,634 A | 6/1988 | Johnson | |
| 4,821,996 A | 4/1989 | Bellotti et al. | |
| 4,988,623 A | 1/1991 | Schwarz et al. | |
| 5,049,273 A | 9/1991 | Knox | |
| 5,301,685 A | 4/1994 | Guirguis | |
| 5,318,510 A | 6/1994 | Cathcart | |
| 5,330,914 A | 7/1994 | Uhlen et al. | |
| 5,336,616 A | 8/1994 | Livesey et al. | |
| 5,372,945 A | 12/1994 | Alchas et al. | |
| 5,409,833 A | 4/1995 | Hu et al. | |
| 5,601,707 A | 2/1997 | Clay et al. | |
| 5,610,074 A | 3/1997 | Beritashvili et al. | |
| 5,624,418 A | 4/1997 | Shepard | |
| 5,785,640 A | 7/1998 | Kresch et al. | |
| 5,786,207 A | 7/1998 | Katz et al. | |
| 5,817,032 A | 10/1998 | Williamson, IV et al. | |
| D401,336 S | 11/1998 | Muller et al. | |
| 5,853,398 A | 12/1998 | Lal et al. | |
| 5,901,717 A | 5/1999 | Dunn et al. | |
| 5,968,356 A | 10/1999 | Morsiani et al. | |
| D424,194 S | 5/2000 | Holdaway et al. | |
| 6,200,606 B1 | 3/2001 | Peterson et al. | |
| 6,258,054 B1 | 7/2001 | Mozsary et al. | |
| 6,261,549 B1 | 7/2001 | Fernandez et al. | |
| 6,478,966 B2 | 11/2002 | Zhou et al. | |
| 6,544,788 B2 | 4/2003 | Singh | |
| 6,623,733 B1 | 9/2003 | Hossainy et al. | |
| 6,733,537 B1 | 5/2004 | Fields et al. | |
| D492,995 S | 7/2004 | Rue et al. | |
| 6,852,533 B1 | 2/2005 | Rafii et al. | |
| 7,147,826 B2 | 12/2006 | Haywood et al. | |
| 7,172,572 B2 | 2/2007 | Diamond et al. | |
| 7,361,368 B2 | 4/2008 | Claude et al. | |
| 7,390,484 B2 | 6/2008 | Fraser et al. | |
| D575,393 S | 8/2008 | Stephens | |
| 7,429,488 B2 | 9/2008 | Fraser et al. | |
| 7,473,420 B2 | 1/2009 | Fraser et al. | |
| 7,501,115 B2 | 3/2009 | Fraser et al. | |
| 7,514,075 B2 | 4/2009 | Hedrick et al. | |
| 7,585,670 B2 | 9/2009 | Hedrick et al. | |
| 7,588,732 B2 | 9/2009 | Buss | |
| 7,595,043 B2 | 9/2009 | Hedrick et al. | |
| 7,651,684 B2 | 1/2010 | Hedrick et al. | |
| 7,687,059 B2 | 3/2010 | Fraser et al. | |
| 7,708,152 B2 | 5/2010 | Dorian et al. | |
| 7,732,190 B2 | 6/2010 | Michal et al. | |
| 7,744,820 B2 | 6/2010 | Togawa et al. | |
| 7,749,741 B2 | 7/2010 | Bullen et al. | |
| 7,780,649 B2 | 8/2010 | Shippert | |
| 7,780,860 B2 | 8/2010 | Higgins et al. | |
| 7,789,872 B2 | 9/2010 | Shippert | |
| 7,794,449 B2 | 9/2010 | Shippert | |
| 7,887,795 B2 | 2/2011 | Fraser et al. | |
| 7,901,672 B2 | 3/2011 | Fraser et al. | |
| 8,062,286 B2 | 11/2011 | Shippert | |
| 8,100,874 B1 | 1/2012 | Jordan et al. | |
| 8,172,818 B2 | 5/2012 | Locke et al. | |
| 8,292,839 B2 | 10/2012 | O'Neill | |
| 8,293,532 B2 | 10/2012 | Moynahan | |
| 8,333,740 B2 | 12/2012 | Shippert | |
| 8,337,711 B2 | 12/2012 | Dorian et al. | |
| 8,366,694 B1 | 2/2013 | Jordan | |
| D679,011 S | 3/2013 | Kitayama et al. | |
| 8,409,860 B2 | 4/2013 | Moynahan | |
| D683,851 S | 6/2013 | Greenhalgh | |
| D687,549 S | 8/2013 | Johnson et al. | |
| D692,559 S | 10/2013 | Scheibel et al. | |
| 8,622,997 B2 | 1/2014 | Shippert | |
| 8,632,498 B2 | 1/2014 | Rimsa et al. | |
| 8,858,518 B2 | 10/2014 | Schafer et al. | |
| 8,887,770 B1 | 11/2014 | Shippert | |
| 9,260,697 B2 | 2/2016 | Cimino et al. | |
| 9,581,942 B1 | 2/2017 | Shippert | |
| 2001/0030152 A1 | 10/2001 | Wright et al. | |
| 2002/0188280 A1 | 12/2002 | Nguyen et al. | |
| 2003/0161816 A1 | 8/2003 | Fraser et al. | |
| 2004/0005246 A1 | 1/2004 | Efthimiadis et al. | |
| 2004/0097867 A1 | 5/2004 | Fraser et al. | |
| 2005/0084961 A1 | 4/2005 | Hedrick et al. | |
| 2005/0131335 A1 | 6/2005 | Drott et al. | |
| 2006/0051865 A1 | 3/2006 | Higgins et al. | |
| 2006/0184119 A1 | 8/2006 | Remde et al. | |
| 2006/0224144 A1 | 10/2006 | Lee | |
| 2007/0106208 A1 | 5/2007 | Uber et al. | |
| 2007/0225665 A1 | 9/2007 | Perez-Cruet et al. | |
| 2007/0248575 A1 | 10/2007 | Connor et al. | |
| 2008/0014181 A1 | 1/2008 | Ariff et al. | |
| 2008/0050275 A1 | 2/2008 | Bischof et al. | |
| 2008/0209709 A1 | 9/2008 | Mayer | |
| 2009/0042267 A1 | 2/2009 | Park | |
| 2009/0181104 A1 | 7/2009 | Rigotti et al. | |
| 2009/0287190 A1 | 11/2009 | Shippert | |
| 2009/0299328 A1 | 12/2009 | Mudd et al. | |
| 2010/0174162 A1 | 7/2010 | Gough et al. | |
| 2010/0268189 A1 | 10/2010 | Byrnes et al. | |
| 2010/0285521 A1 | 11/2010 | Vossman et al. | |
| 2010/0285588 A1 | 11/2010 | Stubbers et al. | |
| 2011/0009822 A1 | 1/2011 | Nielsen | |
| 2011/0117650 A1 | 5/2011 | Riordan | |
| 2011/0198353 A1 | 8/2011 | Tsao | |
| 2012/0003733 A1 | 1/2012 | Gueneron | |
| 2012/0214659 A1 | 8/2012 | Do et al. | |
| 2013/0131635 A1 | 5/2013 | Rimsa et al. | |
| 2013/0150825 A1 | 6/2013 | Rimsa et al. | |
| 2013/0158515 A1 | 6/2013 | Austen, Jr. | |
| 2013/0324966 A1 | 12/2013 | Park et al. | |
| 2014/0363891 A1 | 12/2014 | Llull et al. | |
| 2017/0112976 A1 | 4/2017 | Locke et al. | |
| 2018/0057787 A1 | 3/2018 | Friedman et al. | |

FOREIGN PATENT DOCUMENTS

| | | |
|---|---|---|
| JP | 201112581 A | 1/2011 |
| WO | 2009/055610 A1 | 4/2009 |
| WO | 2011052946 A2 | 5/2011 |
| WO | 2012006587 A2 | 1/2012 |
| WO | 2012/019103 A2 | 2/2012 |
| WO | 2012/083412 A1 | 6/2012 |
| WO | 2012/109603 A1 | 8/2012 |
| WO | 2012/139593 A2 | 10/2012 |
| WO | 2013090579 A1 | 6/2013 |

(56) References Cited

FOREIGN PATENT DOCUMENTS

| WO | 2013106655 A1 | 7/2013 |
| WO | 2014039697 A1 | 3/2014 |

OTHER PUBLICATIONS

Coleman et al.; "Fat Grafting to the Breast Revisited: Safety and Efficacy;" Plastic and Reconstructive Surgery; 119 (3):775-785 (Mar. 2007).

Delay et al.; "Fat Injection to the Breast: Technique, Results and Indications Based on 880 Procedures Over 10 Years;" Aesthetic Surgery Journal; 29(5):360-376 (Sep. 2009-Oct. 2009).

International Preliminary Report on Patentability; dated: Dec. 11, 2014 in the International Patent Application No. PCT/US2013/041111.

Pakhomov et al.; "Hydraulically Coupled Microejection Technique for Precise Local Solution Delivery in Tissues;" J. Neurosci Methods; 155(2):231-240 [Abstract] (Sep. 15, 2006).

Smith et al.; "Autologous Human Fat Grafting: Effect of Harvesting and Preparation Techniques on Adipocyte Graft Survival;" Plastic and Reconstructive Surgery; 117(6):1836-1844 (2006).

Ting et al.; "A New Technique to Assist Epidural Needle Placement;" Anesthesiology; 112(5):1128-1135 (May 2010).

Yoshimura et al.; "Cell-Assisted Lipotransfer for Cosmetic Breast Augmentation: Supportive Use of Adipose-derived Stem/Stromal Cells;" Aesthetic Plastic Surgery Journal; 32:48-55 (2008).

U.S. Appl. No. 15/299,966, filed Oct. 21, 2016, 2017-0112976, Published.

U.S. Appl. No. 15/688,387, filed Aug. 28, 2017, 2018-0057787, Published.

\* cited by examiner

| INPUTS | LIPOSUCTION | HOLD AND MIX | IRRIGATION | VACUUM / CLEAR |
|---|---|---|---|---|
| LIPOSUCTION CANNULA | OPEN | CLOSED | CLOSED | CLOSED |
| IRRIGATION TUBE | CLOSED | CLOSED | OPEN | CLOSED |
| VACUUM TUBE | OPEN | CLOSED | CLOSED | OPEN |
| VENT | CLOSED | CLOSED | OPEN | OPEN |

*FIG. 4*

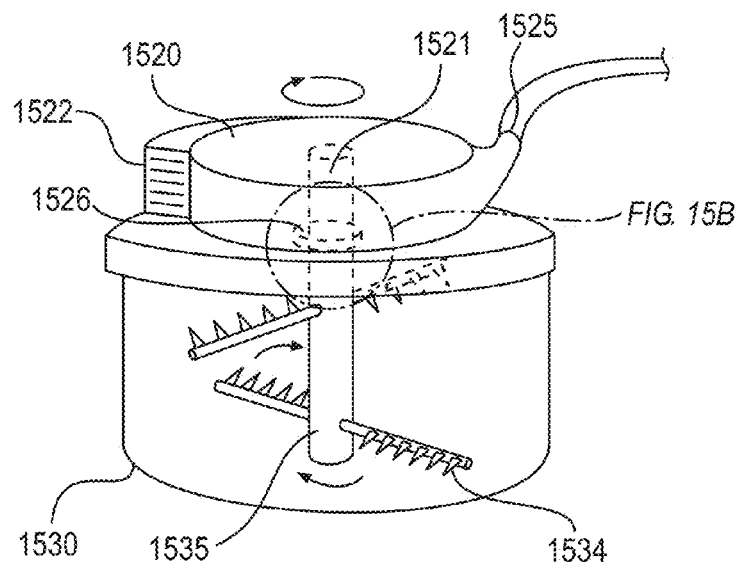
FIG. 15A
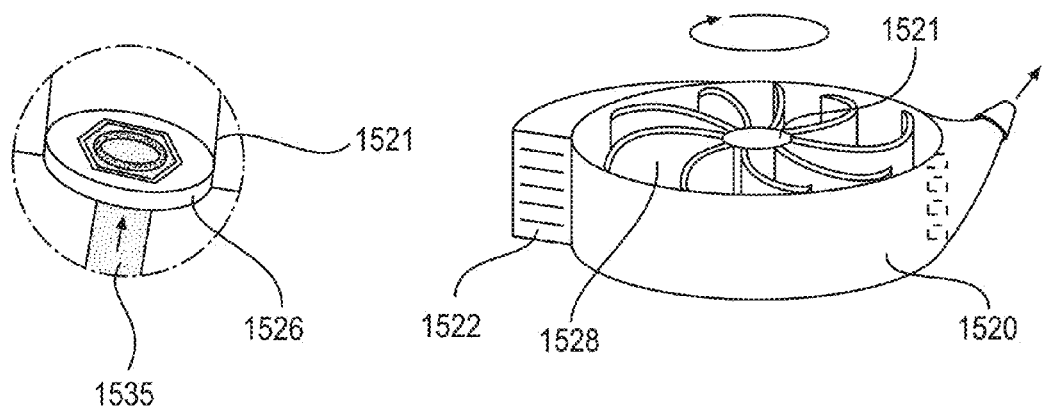
FIG. 15B  FIG. 15C

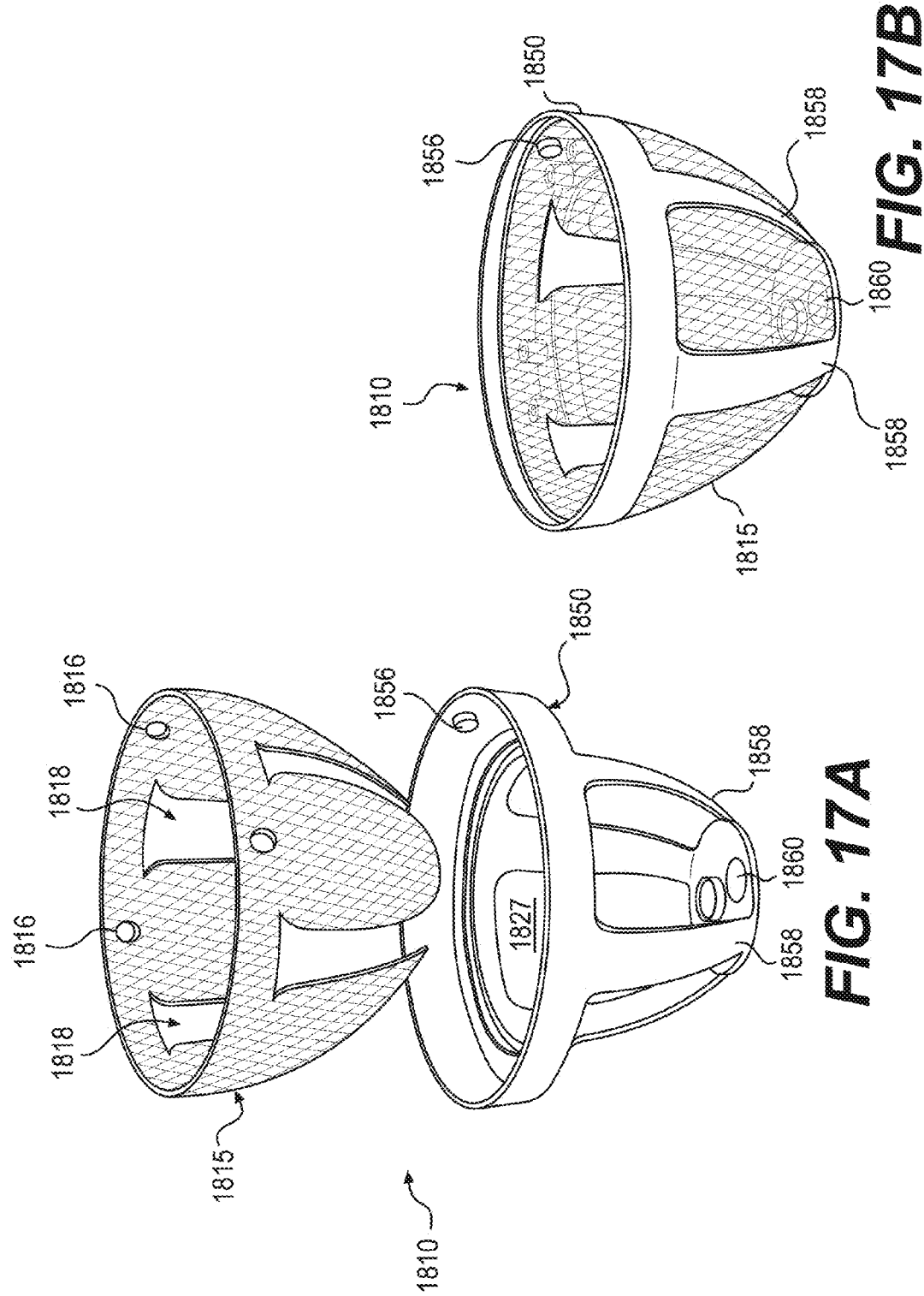

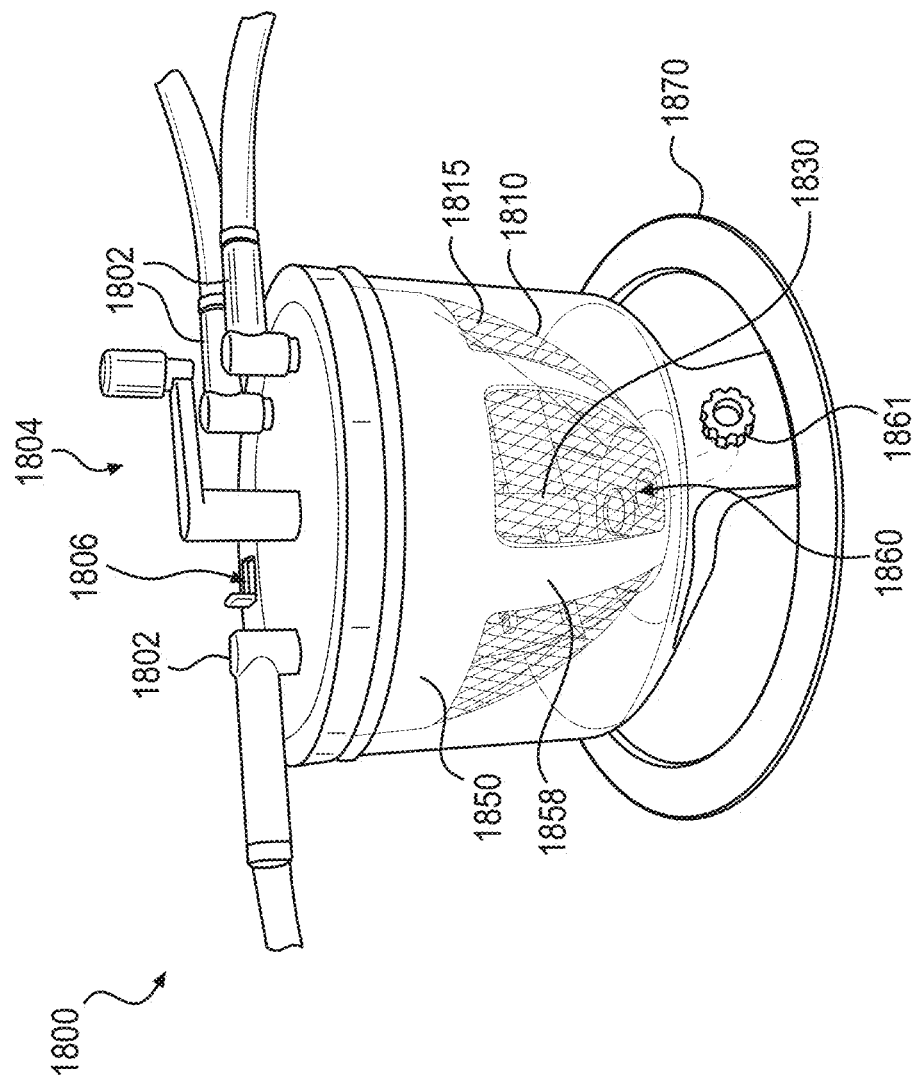

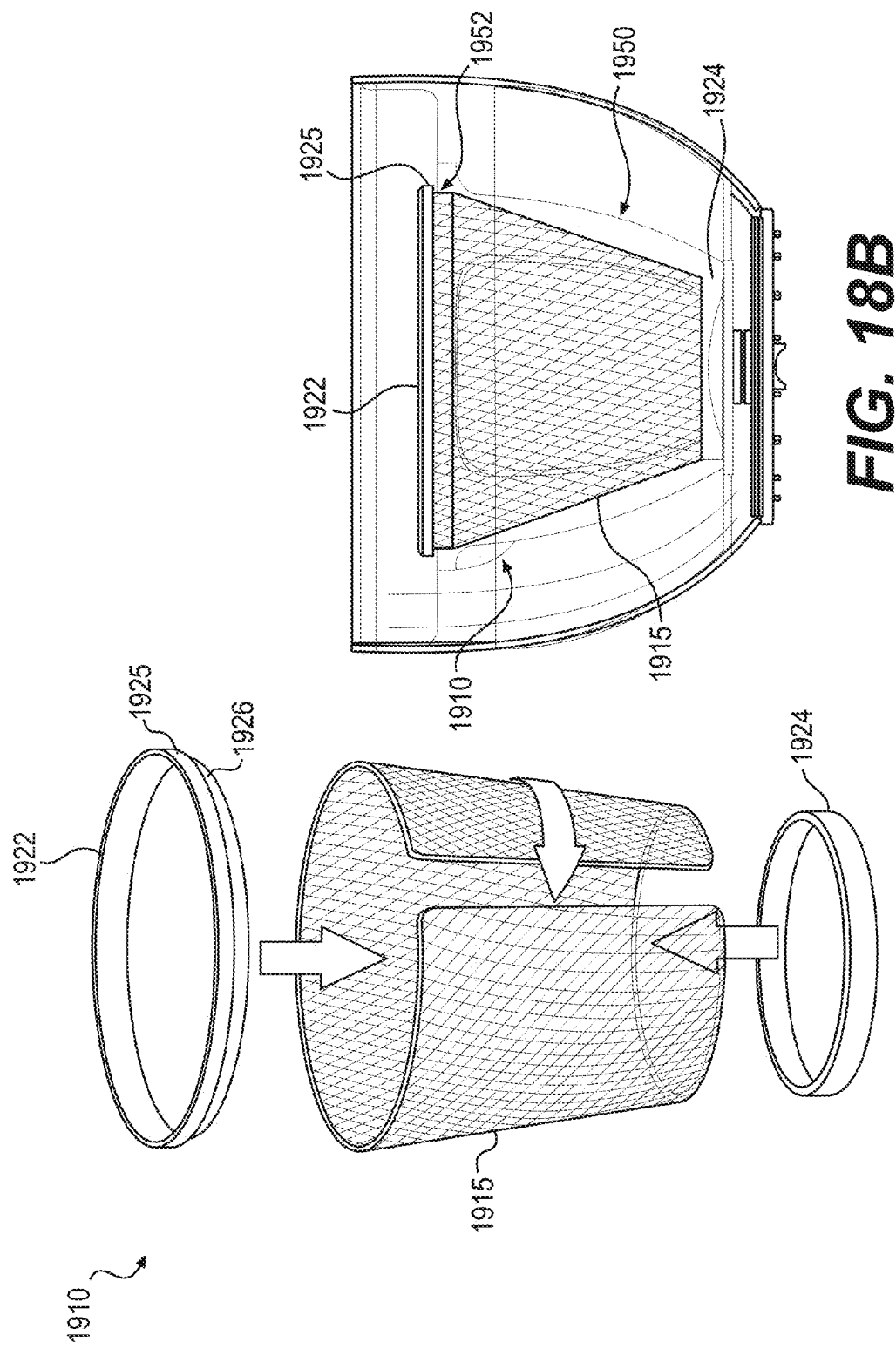

SYSTEMS AND METHODS FOR MEDICAL DEVICE CONTROL

This application claims priority to U.S. Provisional Patent Application 62/244,398, which was filed on Oct. 21, 2015, and U.S. Provisional Patent Application 62/381,116, which was filed on Aug. 30, 2016. Each of the above-referenced applications is incorporated by reference in its entirety.

The present application relates to systems and methods for control of fluid delivery to and from a medical device, including devices for tissue processing and cleaning.

Some surgical procedures require use of tubes, hoses, or other conduits to transfer fluids, gases, and/or tissue products between a patient and a treatment system or device, or among systems and devices. Some surgical procedures are multi-step processes requiring connection and disconnection of hoses from input and output ports. For example, using some adipose tissue transfer systems, surgical personnel may need to perform over one hundred combined user actions and decisions. Some of these user actions involve enabling and disabling a vacuum source or adding or removing tissue or washing solutions to a tissue storage and treatment container.

Keeping track of the state of tube connections in some surgical procedures creates a burden on the practitioner. The user effort needed to manage the tube connections is not negligible and can increase the total time to perform procedures. Although organizational technologies such as color-coding exist, they cannot eliminate the burden of needing to assess the state of each individual tube at multiple points throughout a procedure.

In an embodiment of the present invention, a tissue treatment system includes a container and a flow management device. The container includes an exterior wall surrounding an interior volume for holding tissue. The container also includes a filter structure for processing tissue. The flow management device includes a first plate having a plurality of first openings passing therethrough. The flow management device also includes a second plate having a plurality of second openings passing therethrough. The flow management device also includes a third plate having one or more third openings passing therethrough. The first plate, second plate, and third plate are operably connected. Setting the third plate in a first position places a first subset of the plurality of first openings in fluid communication with a first subset of the plurality of second openings. Setting the third plate in a second position places a second subset of the plurality of first openings in fluid communication with a second subset of the plurality of second openings. Setting the third plate to a third position places a third subset of the plurality of first openings in fluid communication with a third subset of the plurality of second openings.

In an embodiment of the present invention, a flow management device includes a first plate having a plurality of first openings passing therethrough. The flow management device also includes a second plate having a plurality of second openings passing therethrough. The flow management device also includes a third plate having one or more third openings passing therethrough. The first plate, second plate, and third plate are operably connected. Setting the third plate in a first position places a first subset of the plurality of first openings in fluid communication with a first subset of the plurality of second openings. Setting the third plate in a second position places a second subset of the plurality of first openings in fluid communication with a second subset of the plurality of second openings. Setting the third plate to a third position places a third subset of the plurality of first openings in fluid communication with a third subset of the plurality of second openings.

In an embodiment of the present invention, a tissue treatment system includes a container and a tube management device. The container includes an exterior wall surrounding an interior volume for holding tissue and a filter structure for processing tissue. The tube management device includes a tube restrictor plate having a plurality of tube through-holes and a tube stabilizer plate having a plurality of tube through-holes. A plurality of flow-restricting devices is disposed on the tube restrictor plate adjacent to the plurality of tube through-holes. The tube management device further includes a multi-position switch. A plurality of tubes passes through the tube through-holes. Moreover, setting the multi-position switch to a first position causes the plurality of flow-restricting devices to restrict the flow in a first subset of the plurality of tubes to transfer tissue from a patient to the interior volume, setting the multi-position switch to a second position causes the plurality of flow-restricting devices to restrict the flow in a second subset of the plurality of tubes to allow processing of the tissue in the interior volume, and setting the multi-position switch to a third position causes the plurality of flow-restricting devices to restrict the flow in a third subset of the plurality of tubes to allow transfer of the tissue out of the interior volume.

In an embodiment of the present invention, a method of managing surgical conduits is described. The method includes providing a plurality of tubes and a plurality of flow-restricting devices within a device body, each of the flow-restricting devices proximal to at least one of the plurality of tubes. The method also includes providing a multi-position switch wherein flow in a first subset of the plurality of tubes is restricted by the plurality of flow-restricting devices when the multi-position switch is in a first position and flow in a second subset of the plurality of tubes different than the first subset is restricted by the plurality of flow-restricting devices when the multi-position switch is in a second position. The method also includes switching from the first position of the multi-position switch to the second position of the multi-position switch.

In an embodiment of the present invention, a tube management device includes a tube restrictor plate having a plurality of tube through-holes and a tube stabilizer plate having a plurality of tube through-holes. A plurality of flow-restricting devices is disposed on the tube restrictor plate adjacent to the plurality of tube through-holes. The tube management device also includes a multi-position switch and a plurality of tubes that pass through the pluralities of tube through-holes. Setting the multi-position switch of the tube management device to a first position causes the plurality of flow-restricting devices to restrict the flow in a first subset of the plurality of tubes, setting the multi-position switch to a second position causes the plurality of flow-restricting devices to restrict the flow in a second subset of the plurality of tubes, and setting the multi-position switch to a third position causes the plurality of flow-restricting devices to restrict the flow in a third subset of the plurality of tubes.

In an embodiment of the present invention, a tissue treatment system includes a container and a flow management device. The container includes an exterior wall surrounding an interior volume for holding tissue. The container also includes a filter structure for processing tissue. The flow management device includes a first plate having a plurality of first openings passing therethrough. The flow management device also includes a second plate having a plurality of second openings passing therethrough. The first plate and the second plate are operably connected. Setting the first plate in a first position places a first subset of the plurality of first openings in fluid communication with a first subset of the plurality of second openings. Setting the first plate in a second position places a second subset of the plurality of first openings in fluid communication with a second subset of the plurality of second openings. Setting the first plate to a third position places a third subset of the plurality of first openings in fluid communication with a third subset of the plurality of second openings.

In an embodiment of the present invention, a flow management device includes a first plate having a plurality of first openings passing therethrough. The flow management device also includes a second plate having a plurality of second openings passing therethrough. The first plate and the second plate are operably connected. Setting the first plate in a first position places a first subset of the plurality of first openings in fluid communication with a first subset of the plurality of second openings. Setting the first plate in a second position places a second subset of the plurality of first openings in fluid communication with a second subset of the plurality of second openings. Setting the first plate to a third position places a third subset of the plurality of first openings in fluid communication with a third subset of the plurality of second openings.

In an embodiment of the present invention, a flow management device includes a body including a plurality of first openings and a plurality of second openings. The flow management device also includes a multi-position switch. The flow management device also includes a spindle within the body and coupled to the multi-position switch, the spindle including a plurality of third openings. Setting the multi-position switch to a first position places a first subset of the plurality of first openings in fluid communication with a first subset of the plurality of second openings via a first subset of the plurality of third openings. Setting the multi-position switch to a second position places a second subset of the plurality of first openings in fluid communication with a second subset of the plurality of second openings via a second subset of the plurality of third openings. Setting the multi-position switch to a third position places a third subset of the plurality of first openings in fluid communication with a third subset of the plurality of second openings via a third subset of the plurality of third openings.

In an embodiment of the present invention, a flow management device includes a plurality of diaphragm units. Each diaphragm unit includes a flexible diaphragm, a first opening, and a second opening. The diaphragm units have an open position wherein the first opening and second opening are in fluid communication and a closed position wherein the first opening and the second opening are not in fluid communication. The flow management device also includes a rotating plate including one or more protrusions. Each protrusion is capable of pressing against the flexible diaphragm of a diaphragm unit to place the diaphragm unit in the closed position. Rotating the rotating plate to a first position places a first subset of the diaphragm units into the closed position. Rotating the rotating plate to a second position places a second subset of the diaphragm units into the closed position. Rotating the rotating plate to a third position places a third subset of the diaphragm units into the closed position.

In an embodiment of the present invention, a tissue treatment device includes a container. The container includes an exterior wall surrounding an interior volume for holding tissue and a filter structure for processing tissue. The filter structure includes a mesh wall and a frame supporting the mesh wall.

In an embodiment of the present invention, a tissue treatment system includes a container and a flow management device. The container includes an exterior wall surrounding an interior volume for holding tissue and a filter structure for processing tissue. The flow management device includes a first barrier wall having a plurality of first openings passing therethrough. The flow management device includes a second barrier wall having a plurality of second openings passing therethrough. The flow management devices includes a third barrier wall having one or more third openings passing therethrough. The first barrier wall, second barrier wall, and third barrier wall are operably connected. Setting the third barrier wall in a first position places a first subset of the plurality of first openings in fluid communication with a first subset of the plurality of second openings. Setting the third barrier wall in a second position places a second subset of the plurality of first openings in fluid communication with a second subset of the plurality of second openings. Setting the third barrier wall in a third position places a third subset of the plurality of first openings in fluid communication with a third subset of the plurality of second openings.

BRIEF DESCRIPTION OF THE DRAWINGS

FIG. 4 illustrates a decision matrix for determining the status of assorted system inputs in an exemplary tissue transfer system, as described in various embodiments;

FIG. 15A illustrates a tissue treatment system including a turbine in accordance with various embodiments of the present disclosure.

FIG. 15B illustrates a magnified view of a portion of the system of FIG. 15A showing the connection between the turbine and a mount for mixing blades in accordance with various embodiments of the present disclosure.

FIG. 15C illustrates a cutaway view of the turbine incorporated into the system of FIG. 15A in accordance with various embodiments of the present disclosure.

FIGS. 17A and 17B illustrate a disassembled and assembled filter structure, respectively, according to various embodiments of the present disclosure.

FIG. 17C illustrates a tissue treatment system including a filter structure.

FIG. 18A illustrates an exploded view of a conical mesh filter for use in tissue treatment systems according to various embodiments of the present disclosure.

FIG. 18B illustrates placement of the filter of FIG. 18A in a tissue treatment system according to various embodiments of the present disclosure.

DESCRIPTION OF EXEMPLARY EMBODIMENTS

Figure 1:
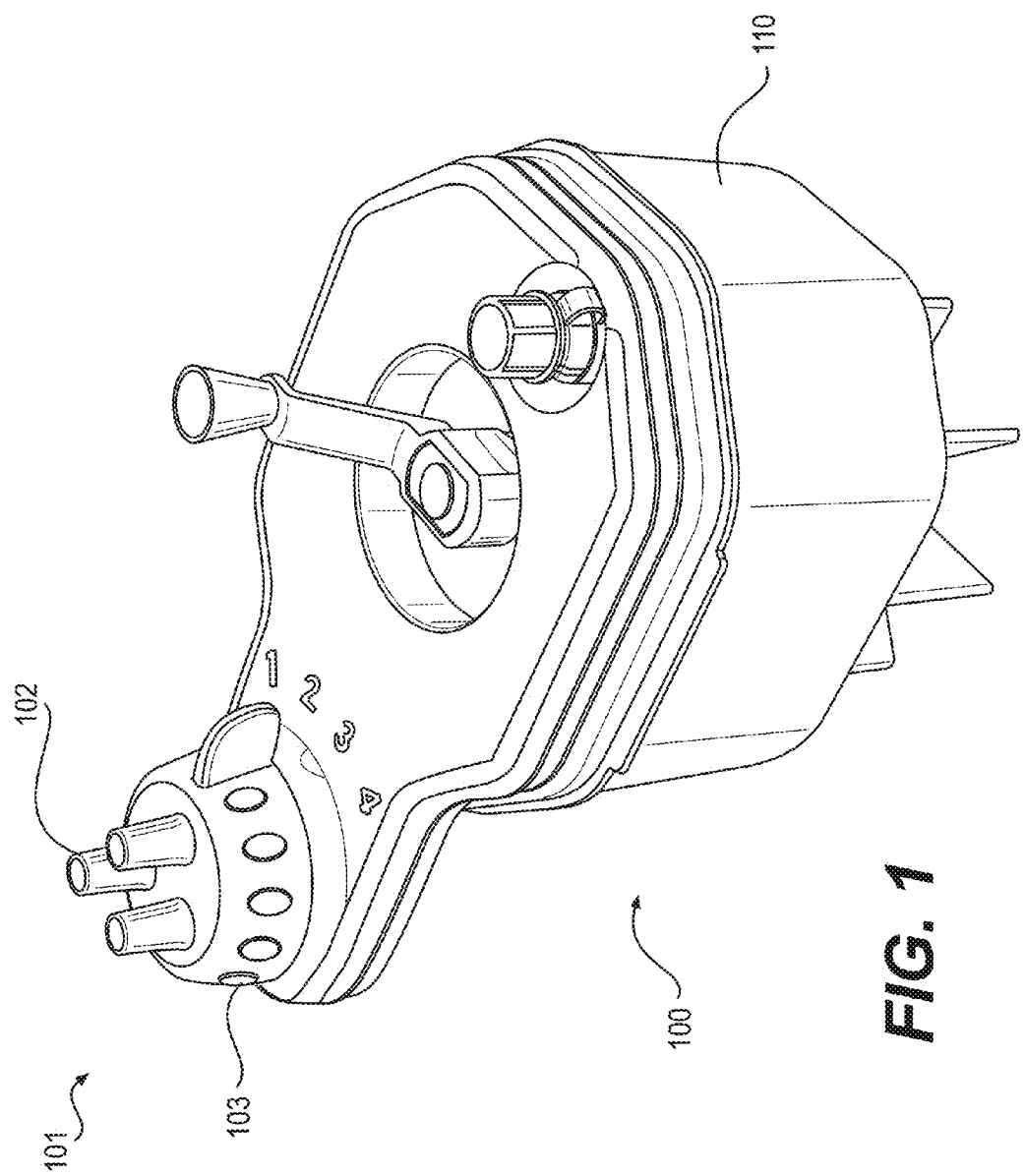
FIG. 1 illustrates a tissue treatment system according to various embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms such as "included" and "includes," is not limiting. The section headings used herein are for organizational purposes only and are not to be construed as limiting the subject matter described. All documents, or portions of documents, cited in this application including but not limited to patents, patent applications, articles, books, and treatises are hereby expressly incorporated by reference in their entirety for any purpose.

As used herein, "adipose tissue" refers to adipose tissue obtained by any means including, for example, liposuction and/or tumescent liposuction. In addition, the adipose tissue may be substantially intact or may be altered by, for example, washing with saline, antimicrobials, detergents, or other agents; the addition of therapeutic agents such an analgesics, antimicrobials, and anti-inflammatories; the removal of some cells or acellular components; or disruption or alteration by the collection process itself including, for example, during liposuction or tumescent liposuction. The adipose tissue can be autologous tissue, allogeneic tissue, or xenogenic tissue (e.g., porcine tissue).

As described above, some surgical procedures require use of tubes, hoses, or other conduits to transfer fluids, gases, and/or tissue products between a patient and a treatment system or device, or among systems and devices. Multi-step procedures are not uncommon and may require connection and disconnection of hoses from input and output ports. For example, a system for adipose tissue transfer and processing (e.g., adipose washing) can require over one hundred combined user actions and decisions, including enabling and disabling vacuum sources or adding or removing tissue or washing solutions to a tissue storage and treatment container. The maintenance and verification of tube connections during a surgical or medical procedure can be non-trivial, especially when the procedure has a time-sensitive component.

Various human and animal tissues can be used to produce products for treating patients. For example, various tissue products have been produced for regeneration, repair, augmentation, reinforcement, and/or treatment of human tissues that have been damaged or lost due to various diseases and/or structural damage (e.g., from trauma, surgery, atrophy, and/or long-term wear and degeneration). Fat grafting, including autologous fat grafting, can be useful for a variety of clinical applications including facial fillers, breast augmentation, buttock augmentation/sculpting, augmentation of other tissue sites, correction of lumpectomy defects, cranial-facial defect correction, and correction of lipoplasty defects (e.g., divots).

To prepare tissue for autologous fat grafting, tissue cleaning and processing must be performed. The process of grafting typically involves steps such as removal of tissue from a patient with a syringe or cannula. The removed tissue is pulled into a tissue processing container where unwanted components of the tissue can be separated and/or the tissue can be cleaned using various solutions. A typical system might include meshes for filtration and separation, cranks connected to mixing blades, and several input and output ports (e.g., to add or remove processing fluids and to transfer tissue). Once the tissue is sufficiently prepared, it must be removed from the container and injected or grafted back into the patient. During transfer steps, vacuum devices help move the tissue from location to location. However, it is desirable to disconnect the vacuum pressure during processing steps. In addition, the tissue-carrying tubes that are not in use during any given step should be blocked to maintain the sterility of the system.

Turning to FIG. 1, an illustrative embodiment of a tissue treatment system 100 is shown. As shown, the tissue treatment system 100 can include a container having an exterior wall 110 surrounding an interior volume. The interior of the container can also contain filters, mixing blades, hoses, and other components to enable washing and conditioning of tissue. The system 100 can include a tube management device 101 to facilitate operation of the system 100. Tubes can pass from the exterior of the system 100 to the interior through ports 102 of the tube management device 101, and tube restrictor devices (discussed below) within the tube management device 101 can control which tubes are open and which are blocked for a given system configuration. The system configuration is determined by the setting of a multi-position switch 103. In some embodiments, the system 100 can be provided with a carry handle for convenient handling by a user. In some embodiments, the tube management device 101 can hold a blocked tube against at least 1 atmosphere (i.e., about 75 cmHg) of vacuum without leaking.

As used herein, the terms "tube," "hose," "conduit," or similar language will be used interchangeably and will be understood to refer to any passageway having a lumen configured to allow passage or fluids, gases, and/or tissue products therethrough.

Figure 2:
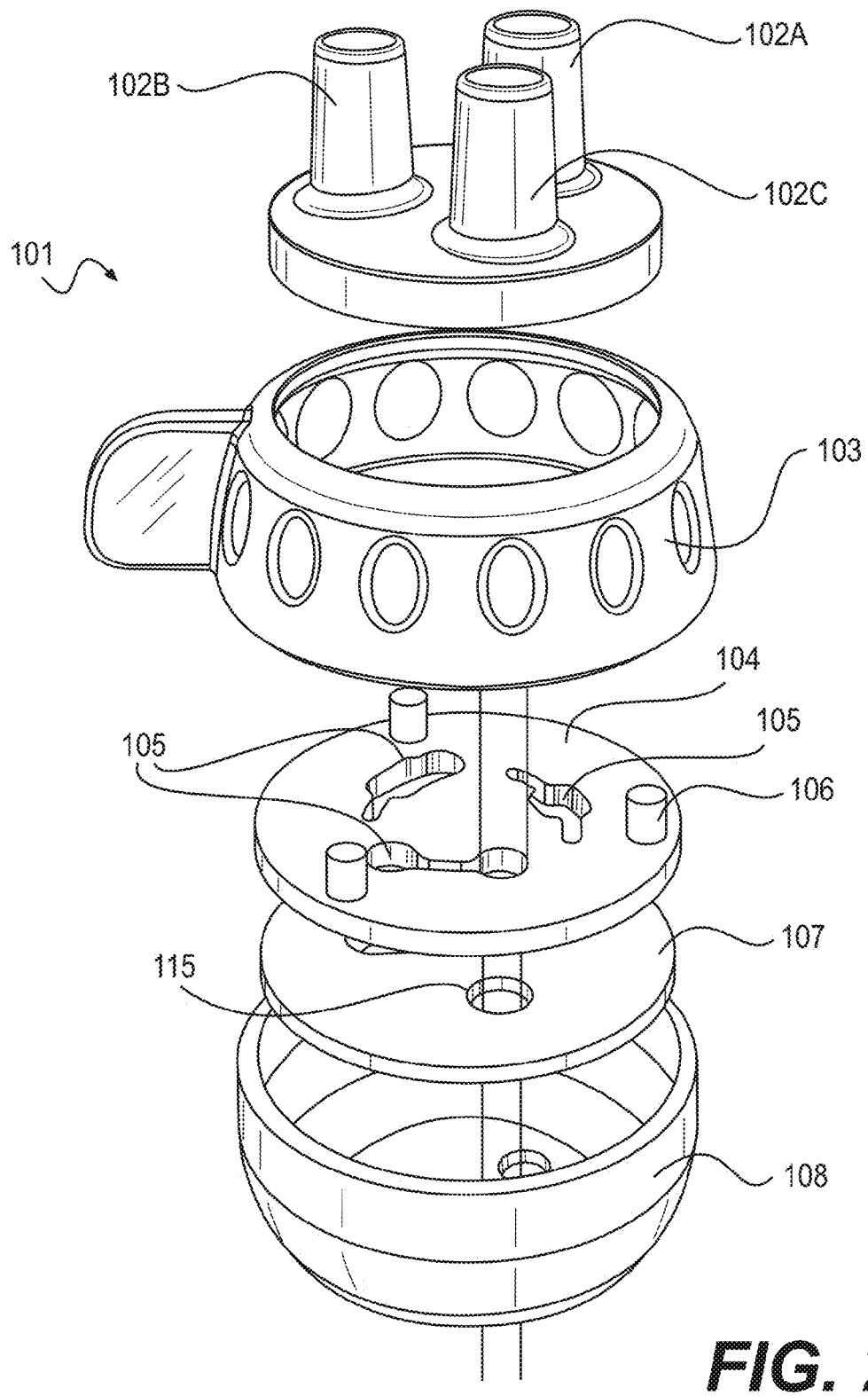
FIG. 2 is an exploded view of a tube management device according to various embodiments.

An exploded view of one embodiment of a tube management device 101 is shown in FIG. 2. The tube management device 101 may include ports 102a, 102b, 102c and a multi-position switch 103. Tubes can pass through the ports 102a, 102b, 102c and then through a tube restrictor plate 104 and a tube stabilizer plate 107 before passing out of the device 101. Based on the position of the multi-position switch 103, restrictor elements 105 on the tube restrictor plate 104 can allow or obstruct flow through each of the tubes. In some embodiments, the contents of the tube management device 101 can be contained within an exterior wall 108 that forms a body. In alternate embodiments, the components of the tube management device 101 can be attached directly to the structure of the container 110.

The ports 102a, 102b, 102c can have a variety of configurations. In accordance with various embodiments, the ports 102a, 102b, 102c may be straight-walled or barbed; threaded or unthreaded; and have no fittings, luer fittings, swaged fittings, or any other type of connector suitable for a specific application. Although the ports 102a, 102b, 102c are depicted as extending out from the body of the tube management device 101, the ports may also be threaded or unthreaded holes or recesses or may extend inward from the surface into the body of the device 101. Although only three ports are depicted in FIG. 2, any number of ports can be chosen to match the number of tubes needed in a particular application. Substances including, but not limited to, gases, liquids, chemical solutions, and biological tissues can flow into or out from the ports 102a, 102b, 102c depending upon the position of the multi-position switch and the requirements of any particular step of the medical procedure.

The position of the multi-position switch 103 can be used to switch among different device configurations. In some embodiments, the multi-position switch 103 is a rotating body or knob, and the rotational angle of the body determines the switch state. In accordance with various embodiments, the multi-position switch 103 may be any mechanical or electronic switch (including rotational or linear throw switches) that, through appropriate linkages, can alter the state of openness of tubes passing through the device. In some embodiments, the multi-position switch 103 can include non-slip grips or similar features to facilitate easier operation by a user, in particular by a user wearing surgical gloves. The positions of the multi-position switch 103 may correspond to steps in a procedure. For example, the steps in a procedure might include liposuction/tissue extraction, hold and mix, irrigation, and vacuum/clear steps.

Figure 3:
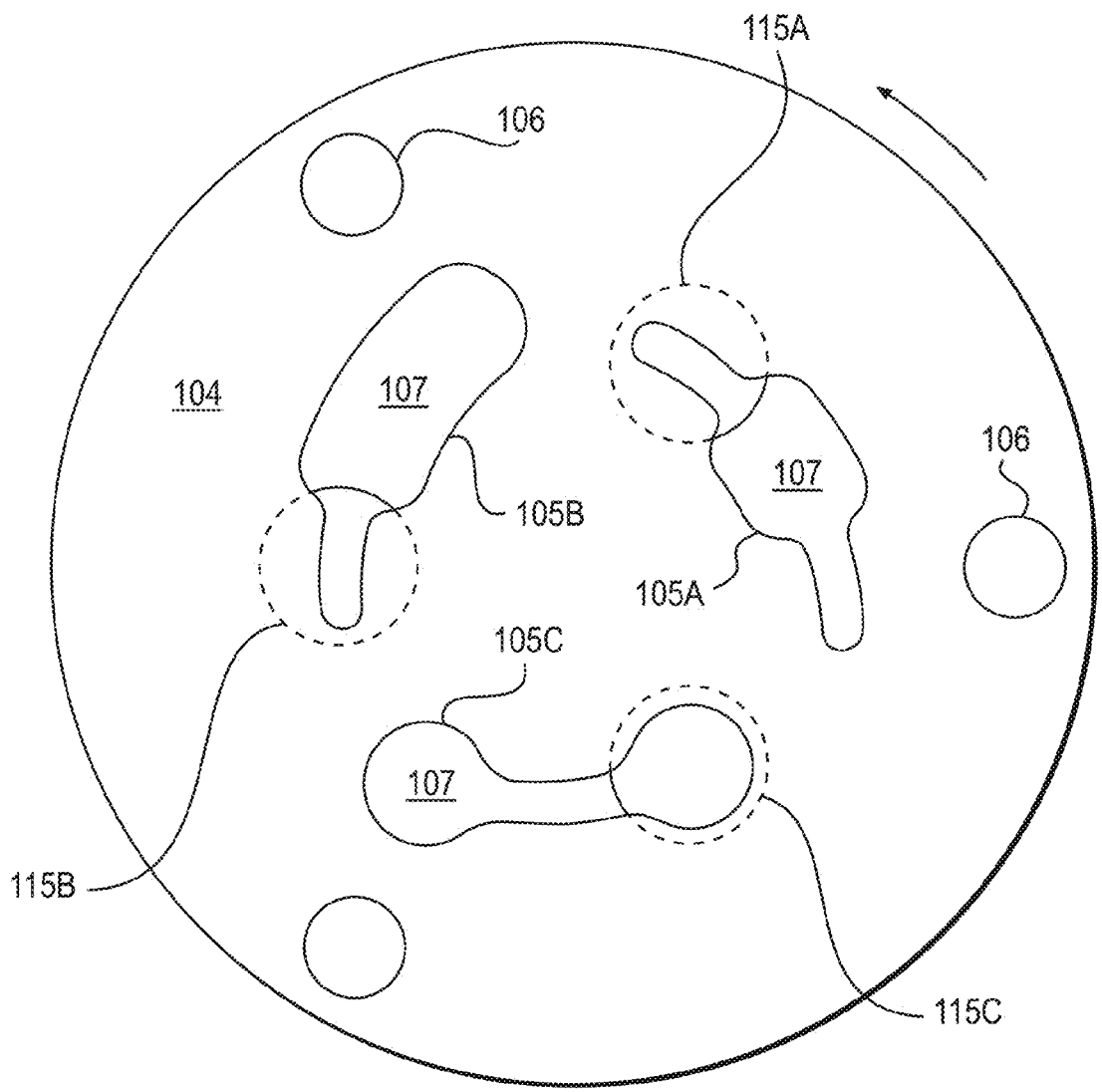
FIG. 3 is a top view of one embodiment of a tube restrictor plate and a tube stabilizer plate, which are components of a tube management system according to the present invention.

The tube restrictor plate 104 can block or allow flow through tubes that pass through the tube through-holes of the plate 104 through the use of flow-restricting devices. In accordance with various embodiments, and as depicted in FIGS. 2 and 3, the tube restrictor plate 104 may be provided with flow-restricting devices 105 in the form of contoured radial slots. The slots 105 can have a slot width that varies according to the desired action of the slot upon a tube for each angular position of the tube restrictor plate 104. For example, each slot 105 may include two slot widths that correspond to either unrestricted flow in a tube or complete blockage of flow in a tube. Alternatively, each slot may have a range of widths corresponding to different levels of flow restriction. In some embodiments, the tube restrictor plate 104 can comprise an acrylic material.

In FIG. 3, a tube restrictor plate 104 is shown overlaid upon a tube stabilizer plate 107 with slots 105a, 105b, 105c indicated. The example embodiment of a tube restrictor plate 104 shown in FIG. 3 illustrates tube through-holes in the form of contoured radial slots 105a, 105b, 105c suitable for a tube management device 101 having a multi-position switch 103 with three positions. The contoured radial slots 105a, 105b, 105c of the tube restrictor plate 104 are overlaid in this top view on the tube through-holes 115a, 115b, 115c of the tube stabilizer plate 107. In this figure, the position of tube restrictor plate 104 with respect to tube stabilizer plate 107 places slots 105a, 105b, 105c in the first position over tube through-holes 115a, 115b, 115c. Activation of the multi-position switch 103 can cause the tube restrictor plate 104 to rotate in the direction shown by the arrow while the tube stabilizer plate 107 stays in place. As a result, the radial slots can advance to the second or third position as needed. In one embodiment, activation of the multi-position switch 103 can cause the tube stabilizer plate 107 to rotate while the tube restrictor plate 104 stays in place. In accordance with various embodiments, the system 100 can be provided with a plurality of tube restrictor plates 104 having different arrangements of slots 105a, 105b, 105c intended for different procedures having different steps. In these embodiments, the user may choose one of the plurality of tube restrictor plates 104 to place within the body 108 of the device 101 depending upon the application.

The tube restrictor plate 104 may have locating features 106 that can interlock with the multi-position switch 103. The locating features 106 can help the user align the tube restrictor plate with the multi-position switch 103 and within the tube management device 101 so that the contoured radial slots 105a, 105b, 105c are properly in-line with their respective ports 102a, 102b, 102c. In addition, the locating features 106 can match with complementary features on the multi-position switch so that the switch's position reflects the proper tubing state within the tube management device 101. In some embodiments, the locating features 106 can fix the multi-position switch 103 to the tube restrictor plate 104 such that they move in concert when the switch is rotated.

The tube management device 101 can have a tube stabilizer plate 107. The tube stabilizer plate 107 may have tube through-holes 115 to allow tubes to pass therethrough. In some embodiments, the diameter of each of the tube through-holes 115 in the tube stabilizer plate 107 may be equal or approximately equal to the outer diameter of the corresponding tube that passes through the hole 115 to provide a secure fit around the outside of each tube without compression. The tube stabilizer plate 107 can hold the tube in position so that activation or movement of the tube restrictor plate 104 cannot twist, reorient, or move the tubes.

As discussed above, the system 100 can be used to operate surgical systems, such as adipose tissue transfer systems. Accordingly, an exemplary decision matrix 400 for an adipose tissue transfer process is shown in FIG. 4. The decision matrix may be used to determine the open/closed status of any tubes in the system during any steps of an adipose transfer procedure. In some embodiments, a tissue treatment system 100 similar to that shown in FIG. 1 can have 4 tube inputs that are either open or blocked during a given step of a medical procedure. In a liposuction or aspiration 402 step, the tube to the liposuction cannula and the vacuum tube may be open while the irrigation tube and vent tube are closed. In a hold and mix or washing 404 step, all 4 inputs can be blocked. In an irrigation or transfer 406 step, the tube to the liposuction cannula and the vacuum tube may be closed while the irrigation tube and the vent tube can be open. In a vacuum/clear 408 step, the tube to the liposuction cannula and the irrigation tube may be closed while the vacuum tube and the vent tube can be open.

Accordingly, and consistent with the decision matrix or foreseeable variations thereof depending on the particular tissue processing being performed, methods of processing adipose tissue are provided. The methods can include at least the following steps, which can be implemented using the various devices described herein and illustrated in any of the disclosed figures. The method can include a first step wherein the device, via a multi-position switch (see, e.g., handle 903 or switch 1003), is set for a liposuction mode, opening a tissue transfer input port and a vacuum port. The method can include a second step, for processing tissue, wherein the switch may be set to a mode for holding and processing (e.g., mixing or incubating) tissue, with all ports likely being closed. The method can further include a third step for irrigation, wherein the multi-position switch is set to allow opening of one or more irrigation or fluid input ports; and a fourth step, for vacuuming (e.g., to remove irrigation or fluid).

It will be appreciated, however, that the various steps may be modified, and/or repeated. For example, multiple irrigation and vacuum/cleaning steps may be performed, and additional ports can be included, as discussed herein.

Figure 5:
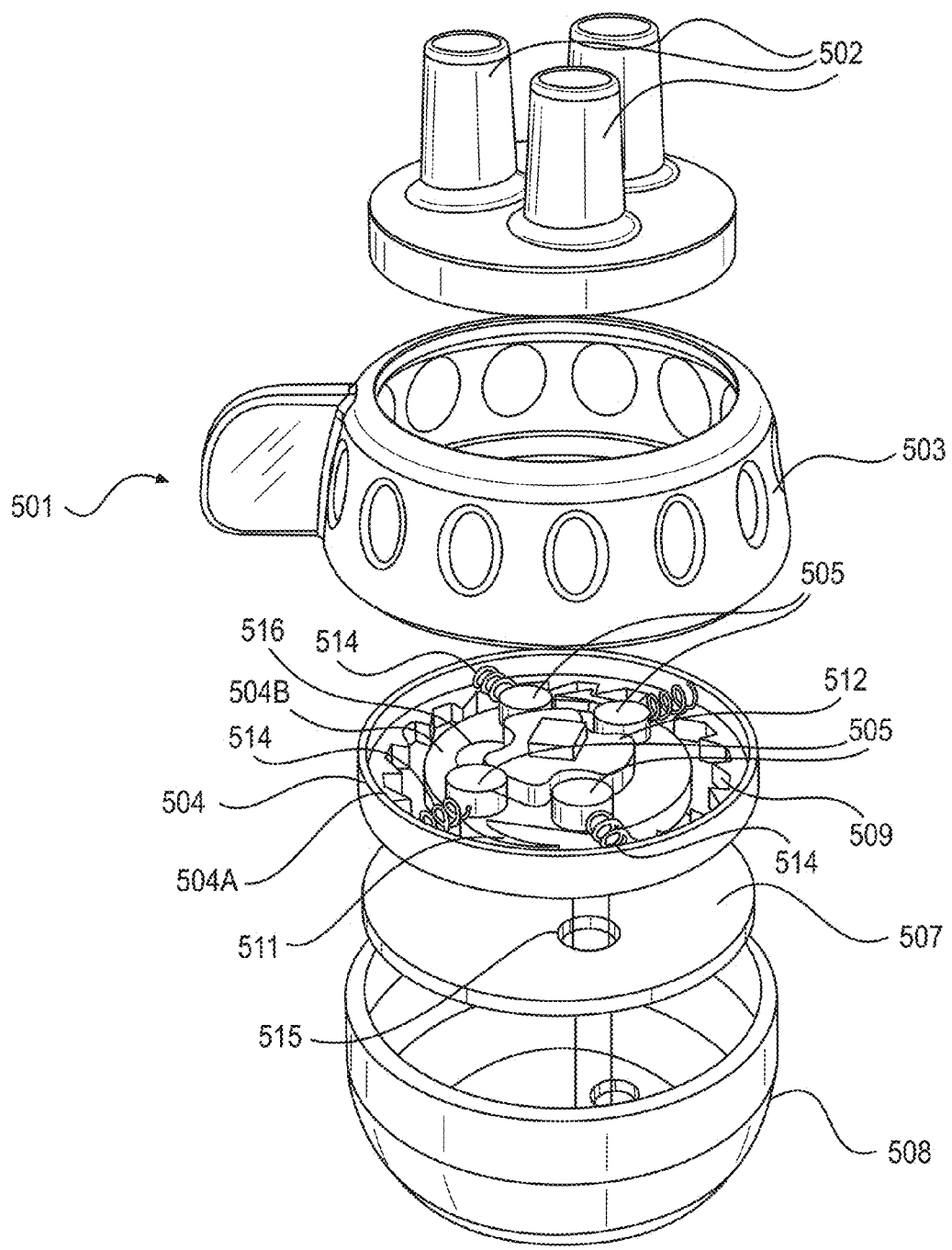
FIG. 5 is an exploded view of an alternative tube management device according to the present invention.

An alternate embodiment of a tube management device 501 is shown in FIG. 5. The tube management device 501 can include ports 502 and a multi-position switch 503. Tubes can pass from the ports 502 through a tube restrictor plate 504 and a tube stabilizer plate 507 before passing out of the device 501. Based on the position of the multi-position switch, restrictor elements 505 on the tube restrictor plate 504 can allow or obstruct flow through each of the tubes. The contents of the tube management device 501 can be contained within an exterior wall 508 that forms a body.

As with the previously discussed embodiments, the ports can have a variety of configurations. For example, the ports 502 may be straight-walled or barbed; threaded or unthreaded; and have no fittings, luer fittings, swaged fittings, or any other type of connector demanded by application-specific requirements. Although the ports 502 are depicted in this embodiment as extending out from the body of the tube management device 501, the ports may also be threaded or unthreaded recesses or holes or may extend inward from the device surface into the body of the device 501. Although only three ports are depicted in FIG. 5, any number of ports can be chosen to match the number of tubes needed in a particular application. Substances including, but not limited to, gases, liquids, chemical solutions, and biological tissues can flow into or out from the ports 502 depending upon the position of the multi-position switch and the requirements of any particular step of the surgical procedure.

The positions of the multi-position switch 503 can be used to switch among different device configurations. In some embodiments, the multi-position switch 503 is a rotating body or knob and the rotational angle of the body determines the switch state. In accordance with various embodiments, the multi-position switch 503 may be any mechanical or electronic switch (including rotational or linear throw switches) that, through appropriate linkages, can alter the state of openness of tubes passing through the device. In some embodiments, the multi-position switch 503 can include non-slip grips or similar features to facilitate easier operation by a user, in particular by a user wearing surgical gloves. The positions of the multi-position switch 503 may correspond to steps in a procedure. For example, the steps in a procedure might include liposuction/tissue extraction, hold and mix, irrigation, and vacuum/clear steps.

The tube restrictor plate 504 can block or allow flow through the tubes that pass through the tube through-holes 516 of the plate through the use of flow-restricting devices. The tube restrictor plate 504 may include an external ring 504a that is rotatably engaged with a central portion 504b. Tubes can pass through the tube restrictor plate 504 through tube through-holes 516 adjacent to flow-restricting devices. In accordance with various embodiments and as depicted in FIG. 5, the tube restrictor plate 504 may be provided with flow-restricting devices in the form of a contoured central hub 512 on the central portion 504b and sliding blocks 505 that force the tubes against the hub 512 via the integrated springs 514 attached to the external ring 504a. The sliding blocks 505 may be shaped as flat plates, cylinders, ovals, spheres, ovoid configuration, or any other shape that meets application-specific requirements. In some embodiments, the contoured central hub 512 may have an equal number of recesses to the number of ports 502, and each tube may pass through a tube through-hole 516 adjacent to a recess of the contoured central hub. When a sliding block 505 attached to an integrated spring 512 is in line with a recess of the contoured central hub 512, the force of the spring may extend the sliding block and force it against a tube. In some embodiments, the central portion 504b of the tube restrictor plate 504 may be fixedly attached to the tube stabilizer plate 507. As the multi-position switch 503 changes from one position to another, the external ring 504a of the tube restriction plate 504 may rotate while the central portion 504b containing the contoured central hub 512 does not rotate relative to the tube stabilizer plate 507.

In accordance with various embodiments, the external ring 504a may be provided with a one-way ratcheting mechanism 509. The teeth of the ratcheting mechanism can engage with a pawl 511 positioned on the central portion 504b of the tube restriction plate 504 such that rotation of the external ring 504a is allowed in one direction but prevented in the opposite direction. Although the pawl 511 is depicted as being located on the central portion 504b in this embodiment, it will be apparent to those of ordinary skill in the art that the pawl could be attached at other points throughout the tube management device 501 such as the interior of the multi-position switch 503 or the tube stabilizer plate 507.

The tube management device 501 can also include a tube stabilizer plate 507. The tube stabilizer plate 507 may have tube through-holes 515 to allow tubes to pass through. In some embodiments, the diameter of each of the tube through-holes 515 in the tube stabilizer plate 507 may be equal to or slightly greater than the outer diameter of the corresponding tube that passes through the hole to provide a secure fit around the outside of each tube without compression. The tube stabilizer plate 507 can hold the tube in position so that activation or movement of the tube restrictor plate 504 cannot twist, reorient, or move the tubes.

Figure 6:
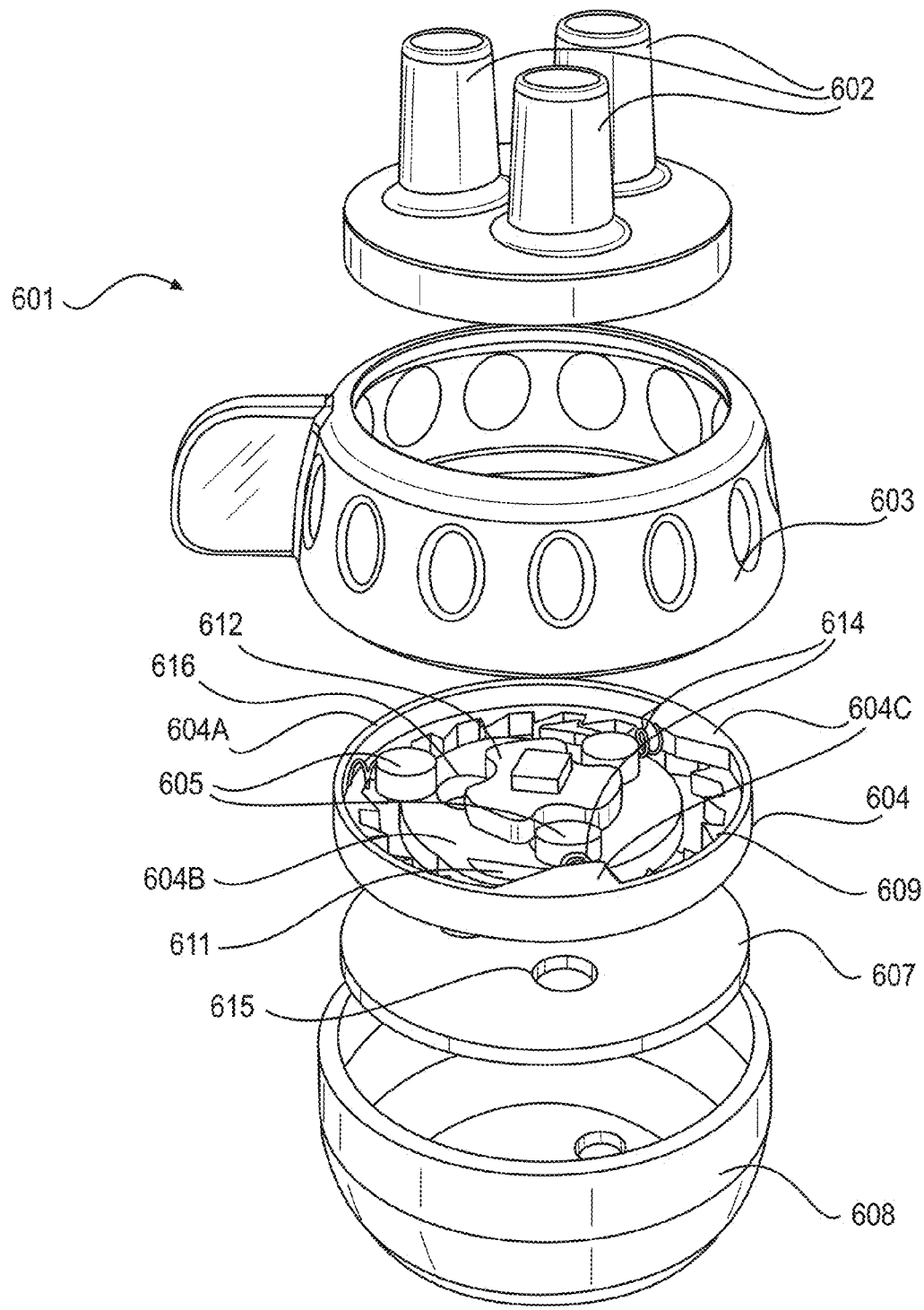
FIG. 6 illustrates a variant of the tube management device displayed in FIG. 5, according to various embodiments.

Another embodiment of a tube management device is shown in FIG. 6. The tube management device 601 can include ports 602 and a multi-position switch 603. The device 601 can include a tube stabilizer plate 607 and a tube restrictor plate 604 containing flow restriction devices. The components of the device 601 can be enclosed within a body 608.

The ports 602 are the connection between the tube management device 601 and the exterior world. In accordance with various embodiments, the ports 602 may be straight-walled or barbed; threaded or unthreaded; and have no fittings, luer fittings, swaged fittings, or any other type of connector demanded by application-specific requirements. Although the ports 602 are depicted in this embodiment as extending out from the body of the tube management device 601, the ports may also be threaded or unthreaded holes or may extend inward from the device surface into the body of the device 601. Although only three ports are depicted in FIG. 6, it will be evident to one of ordinary skill in the art that any number of ports 602 can be chosen to match the number of tubes needed in a particular application. Fluids including, but not limited to, gases, liquids, chemical solutions, and biological tissues can flow into or out from the ports 602 depending upon the position of the multi-position switch and the requirements of any particular step of the medical procedure.

The positions of the multi-position switch 603 can be used to switch among different device configurations. In some embodiments, the multi-position switch 603 is a rotating body or knob and the rotational angle of the body determines the switch state. In accordance with various embodiments, the multi-position switch 603 may be any mechanical or electronic switch (including rotational or linear throw switches) that, through appropriate linkages, can alter the state of openness of tubes passing through the device. In some embodiments, the multi-position switch 603 can include non-slip grips or similar features to facilitate easier operation by a user, in particular by a user wearing surgical gloves. The positions of the multi-position switch 603 may correspond to steps in a procedure. For example, the steps in a procedure might include liposuction/tissue extraction, hold and mix, irrigation, and vacuum/clear steps.

The tube restrictor plate 604 may include an external ring 604a that is rotatably engaged with a central portion 604b. Tubes may pass through tube through-holes 616 adjacent to flow-restricting devices. In accordance with various embodiments and as depicted in FIG. 6, the tube restrictor plate 604 may be provided with flow-restricting devices in the form of a contoured central hub 612 on the central portion 604b and sliding blocks 605 that force the tubes against the hub 612 via the integrated springs 614 attached to the external ring 604a. The sliding blocks 605 may be shaped as flat plates, cylinders, ovals, spheres, eggs, or any other shape that meets application-specific requirements. In some embodiments, the contoured central hub 612 may have an equal number of recesses to the number of ports 602, and each tube may pass through a tube through-hole 616 adjacent to a recess of the contoured central hub. When a sliding block 605 attached to an integrated spring 612 is in line with a recess of the contoured central hub 612, the force of the spring may extend the sliding block and force it against a tube. As the multi-position switch 603 changes from one position to another, the external ring 604a of the tube restriction plate 604 may rotate while the central portion 604b containing the contoured central hub 612 does not rotate relative to the tube stabilizer plate 607. In accordance with various embodiments, the sliding blocks 605 and integrated springs 614 can be placed at different radial depths using spacers 604c.

The tube management device 601 can have a tube stabilizer plate 607 in some embodiments. The tube stabilizer plate 607 may have tube through-holes 615 to allow tubes to pass through. In preferred embodiments, the diameter of each of the tube through-holes 615 in the tube stabilizer plate 607 may be equal to the outer diameter of the corresponding tube that passes through the hole to provide a secure fit around the outside of each tube without compression. The tube stabilizer plate 607 can hold the tube in position so that activation or movement of the tube restrictor plate 604 cannot twist, reorient, or move the tubes.

Figure 7:
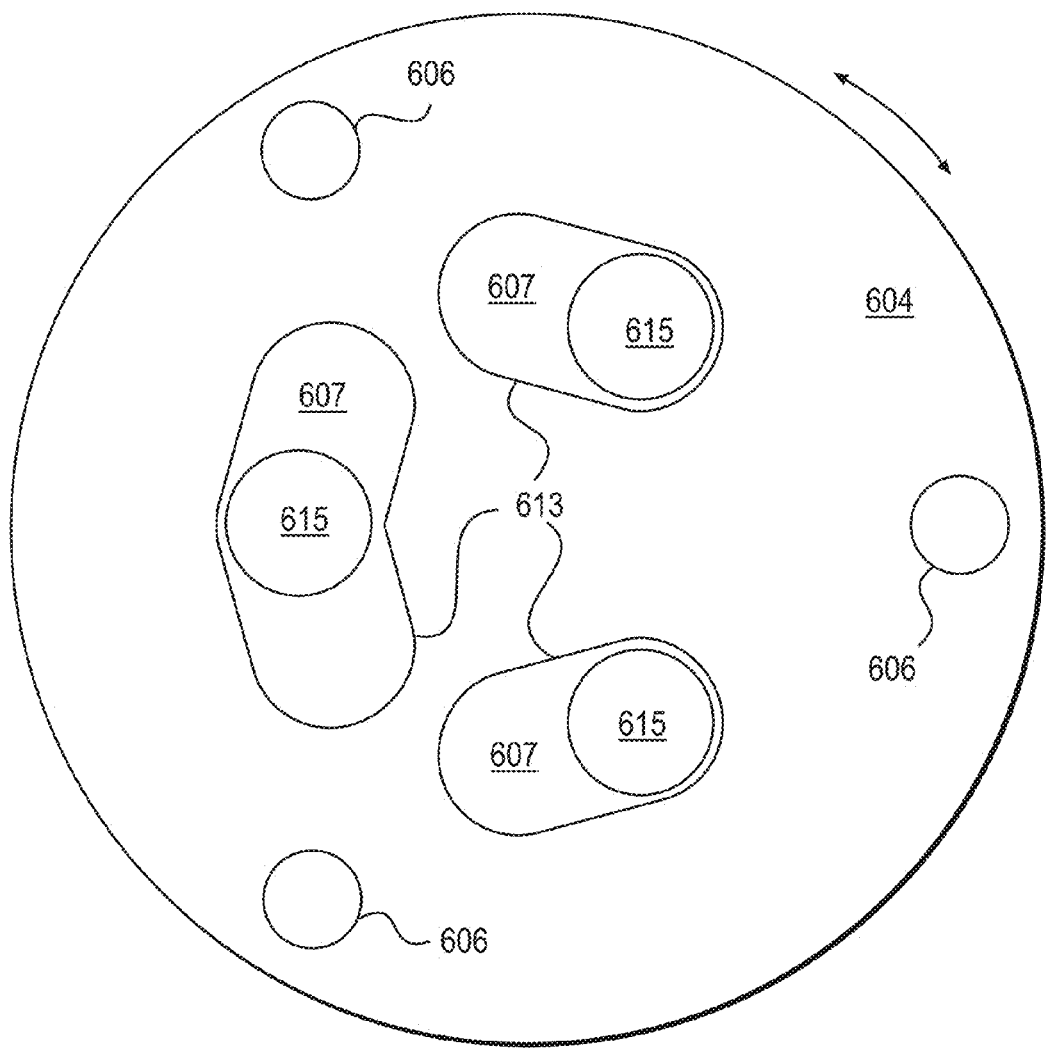
FIG. 7 is a top view of a tube restrictor plate and a tube stabilizer plate of the tube management device of the embodiment shown in FIG. 6.

A top view of the tube restrictor plate 604 overlaid on tube stabilizer plate 607 of the embodiment of FIG. 6 is shown in FIG. 7. In accordance with various embodiments, the tube restrictor plate 604 can have slots 613 to allow the tubes to change position with respect to the contoured central hub 612 of the central portion 604b and the associated flow-restricting devices. In this way, a single embodiment of the tube restrictor plate 604 can be used in more than one configuration. When a tube is in an "in" position, the tube passes near a recess of the contoured central hub 612 and can be closed by sliding blocks 605 attached to spacers 604c extending from the external ring 604a. When a tube is in an "out" position, the tube passes near an extended portion of the contoured central hub 612. In this position, the tube can be closed by sliding blocks 605 that are attached by integrated springs 614 directly to the external ring 604a. In a preferred embodiment, sliding blocks 605 attached directly to the external ring 604a without spacers 604c cannot reach tubes adjacent to recesses of the contoured central hub 612.

In accordance with various embodiments, the external ring 604a may be provided with a one-way ratcheting mechanism 609. The teeth of the ratcheting mechanism can engage with a pawl 611 positioned on the central portion 604b of the tube restriction plate 604 such that rotation of the external ring 604a is allowed in one direction but prevented in the opposite direction. Although the pawl 611 is depicted as being located on the central portion 604b in this embodiment, it will be apparent to those of ordinary skill in the art that the pawl could be attached at other points throughout the tube management device 601 such as the interior of the multi-position switch 603 or the tube stabilizer plate 607.

A method of managing surgical conduits is also envisioned by the inventors. The method includes providing several tubes and several flow-restricting devices within a body where each of the flow-restricting devices is proximal to at least one of the tubes and providing a multi-position switch wherein the flow in a first subset of the tubes is restricted by the flow-restricting devices when the switch is in a first position and flow in a second subset of tubes different than the first subset is restricted by the flow-restricting devices when the switch is in a second position. The method can further include switching from the first position of the multi-position switch to the second position.

The step of providing several tubes and several flow-restricting devices within a body where each of the flow-restricting devices is proximal to at least one of the tubes may include, but is not limited to, passing tubes through ports 102 and past flow-restricting devices 105 in a tube management device 101 as described above in connection with FIGS. 1-3.

The step of providing a multi-position switch wherein the flow in a first subset of the tubes is restricted by the flow-restricting devices when the switch is in a first position and flow in a second subset of tubes different than the first subset is restricted by the flow-restricting devices when the switch is in a second position may include, but is not limited to, providing a multi-position switch 103 in a tube management device 101 as described above in connection with FIGS. 1-3.

The step of switching from the first position of the multi-position switch to the second position may include, but is not limited to, switching a multi-position switch 103 from a first position to a second position as described above in connection with FIGS. 1 and 2.

Figure 8:
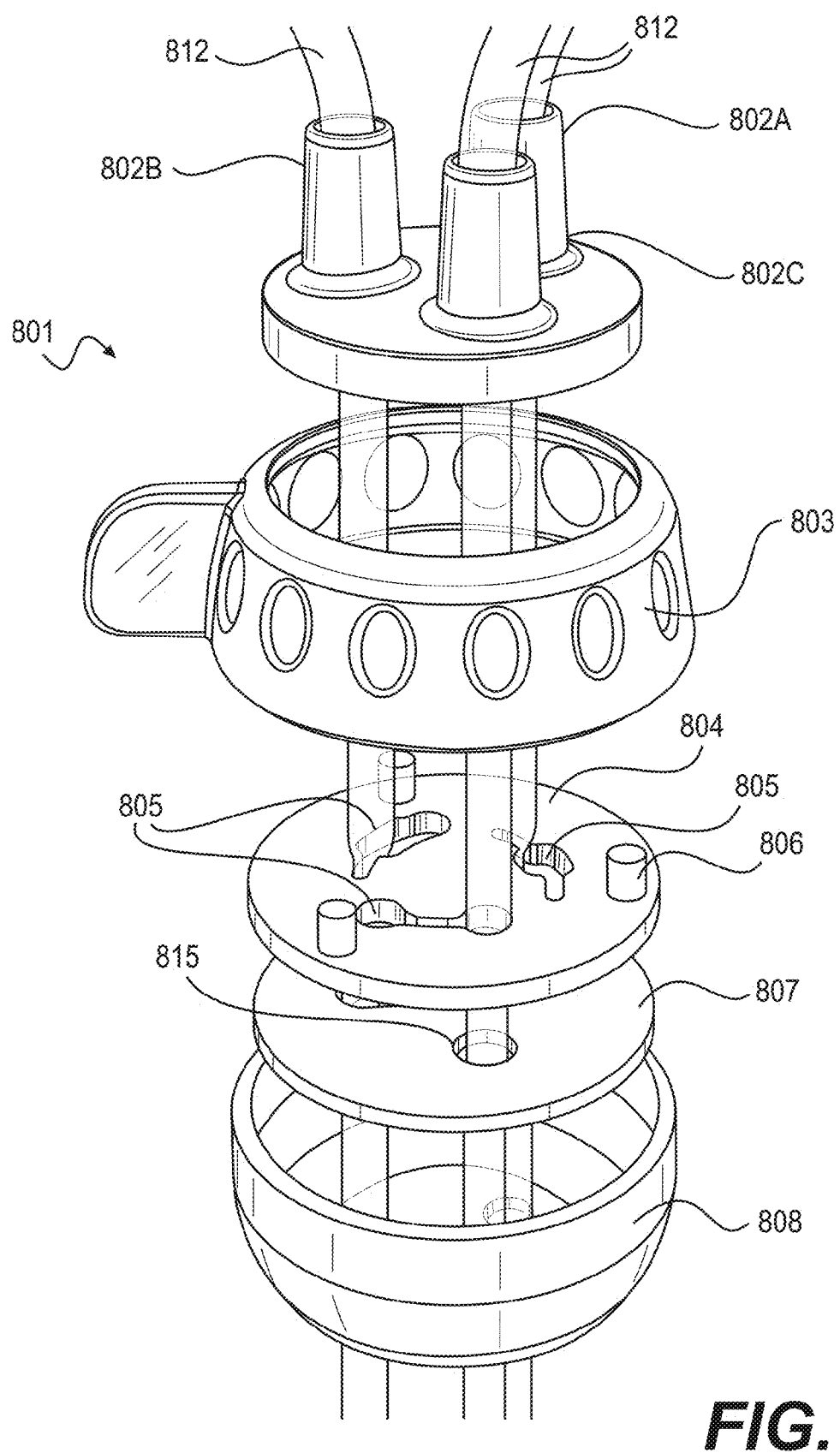
FIG. 8 illustrates a tube management device according to various embodiments.

An exploded view of an alternative embodiment of a tube management device 801 is shown in FIG. 8. The tube management device 801 may include ports 802a, 802b, 802c and a multi-position switch 803. Tubes 812 pass through the ports 802a, 802b, 802c and then through a tube restrictor plate 804 and a tube stabilizer plate 807 before passing out of the device 801. Based on the position of the multi-position switch 803, restrictor elements 805 on the tube restrictor plate 804 can allow or obstruct flow through each of the tubes 812. In some embodiments, the contents of the tube management device 801 can be contained within an exterior wall 808 that forms a body.

The ports 802a, 802b, 802c can have a variety of configurations as described previously with respect to FIG. 2. In accordance with various embodiments, the ports 802a, 802b, 802c may be straight-walled or barbed; threaded or unthreaded; and have no fittings, luer fittings, swaged fittings, or any other type of connector suitable for a specific application. Although the ports 802a, 802b, 802c are depicted as extending out from the body of the tube management device 801, the ports may also be threaded or unthreaded holes or recesses or may extend inward from the surface into the body of the device 801. Although only three ports are depicted in FIG. 8, any number of ports can be chosen to match the number of tubes 812 needed in a particular application. Substances including, but not limited to, gases, liquids, chemical solutions, and biological tissues can flow into or out of tubes 812 passing through the ports 802a, 802b, 802c depending upon the position of the multi-position switch and the requirements of any particular step of a medical procedure.

As described above with reference to FIG. 2, the position of the multi-position switch 803 can be used to switch among different device configurations. In some embodiments, the multi-position switch 803 is a rotating body or knob, and the rotational angle of the body determines the switch state. In accordance with various embodiments, the multi-position switch 803 may be any mechanical or electronic switch (including rotational or linear throw switches) that, through appropriate linkages, can alter the state of openness of the tubes 812. In some embodiments, the multi-position switch 803 can include non-slip grips or similar features to facilitate easier operation by a user, in particular by a user wearing surgical gloves. The positions of the multi-position switch 803 may correspond to steps in a procedure. For example, the steps in a procedure might include liposuction/tissue extraction, hold and mix, irrigation, and vacuum/clear steps.

The tube restrictor plate 804 can block or allow flow through the tubes 812 as they pass through the plate through the use of flow-restricting devices. Similar to the embodiments depicted in FIGS. 2 and 3, the tube restrictor plate 804 may be provided with both flow-restricting devices and tube through-holes in the form of contoured radial slots 805. In alternative embodiments, the flow-restricting devices can be similar to those described above with reference to the embodiments of FIGS. 5 and 6. The slots 805 can have a slot width that varies according to the desired action of the slot upon a tube 812 for each angular position of the tube restrictor plate 804. For example, each slot 805 may include two slot widths that correspond to unrestricted flow in a tube 812 and complete blockage of flow in a tube 812. Alternatively, each slot may have a range of widths corresponding to different levels of flow restriction.

The tube restrictor plate 804 may have locating features 806 that can interlock with the multi-position switch 803. The locating features 806 can help the user align the tube restrictor plate 804 with the multi-position switch 803 and within the tube management device 801 so that the contoured radial slots 805 are properly in-line with their respective ports 802a, 802b, 802c. In addition, the locating features 806 can match with complementary features on the multi-position switch so that the switch's position reflects the proper tubing state within the tube management device 801. In some embodiments, the locating features 806 can fix the multi-position switch 803 to the tube restrictor plate 804 such that they move in concert when the switch is rotated.

The tube management device 801 can have a tube stabilizer plate 807. The tube stabilizer plate 807 may have tube through-holes 815 to allow tubes to pass therethrough. In some embodiments, the diameter of each of the tube through-holes 815 in the tube stabilizer plate 807 may be equal or approximately equal to the outer diameter of the corresponding tube that passes through the hole to provide a secure fit around the outside of each tube without compression. The tube stabilizer plate 807 can hold the tube in position so that activation or movement of the tube restrictor plate 804 cannot twist, reorient, or move the tubes.

The tubes 812 of tube management device 801 can be made of any material that meets application-specific requirements. The tubes 812 may be made of, for example but not limited to, PVC, high-density polyethylene, nylon, latex, silicone, polyurethane, TYGON®, or any non-reactive tubing or hose. As depicted in FIG. 8, the tubes 812 may extend out of the ports 802a, 802b, 802c or may terminate within or below the ports 802a, 802b, 802c. The tubes 812 may be permanently attached to the tube management device 801, for example, at the ports 802a, 802b, 802c or body 808, or the tubes 812 may be removable and/or replaceable. In accordance with various embodiments, the tubes 812 may be disposed of after each procedure and replaced with new tubes 812 to allow for reuse of tube management device 801 for multiple procedures.

The embodiments described above include tube management devices that are operable to release or constrict flow within tubes depending upon the configuration of the device. In addition to tube management devices, flow management devices taught herein can allow or interrupt flow between a plurality of first openings and a plurality of second openings. The first and second openings can be connected to fluid ports or tubes to carry liquids, gases, or biological material. In some embodiments, the first openings and the second openings can be defined in stationary or movable walls, plates, or other barrier materials that otherwise prevent the passage of liquids, gases, or biological material. In addition, the various embodiments can be combined and interchanged, e.g., using combinations of tube management devices described above and the systems for controlling flow through various openings. Several embodiments and implementations of flow management devices are described below.

Figure 9A:
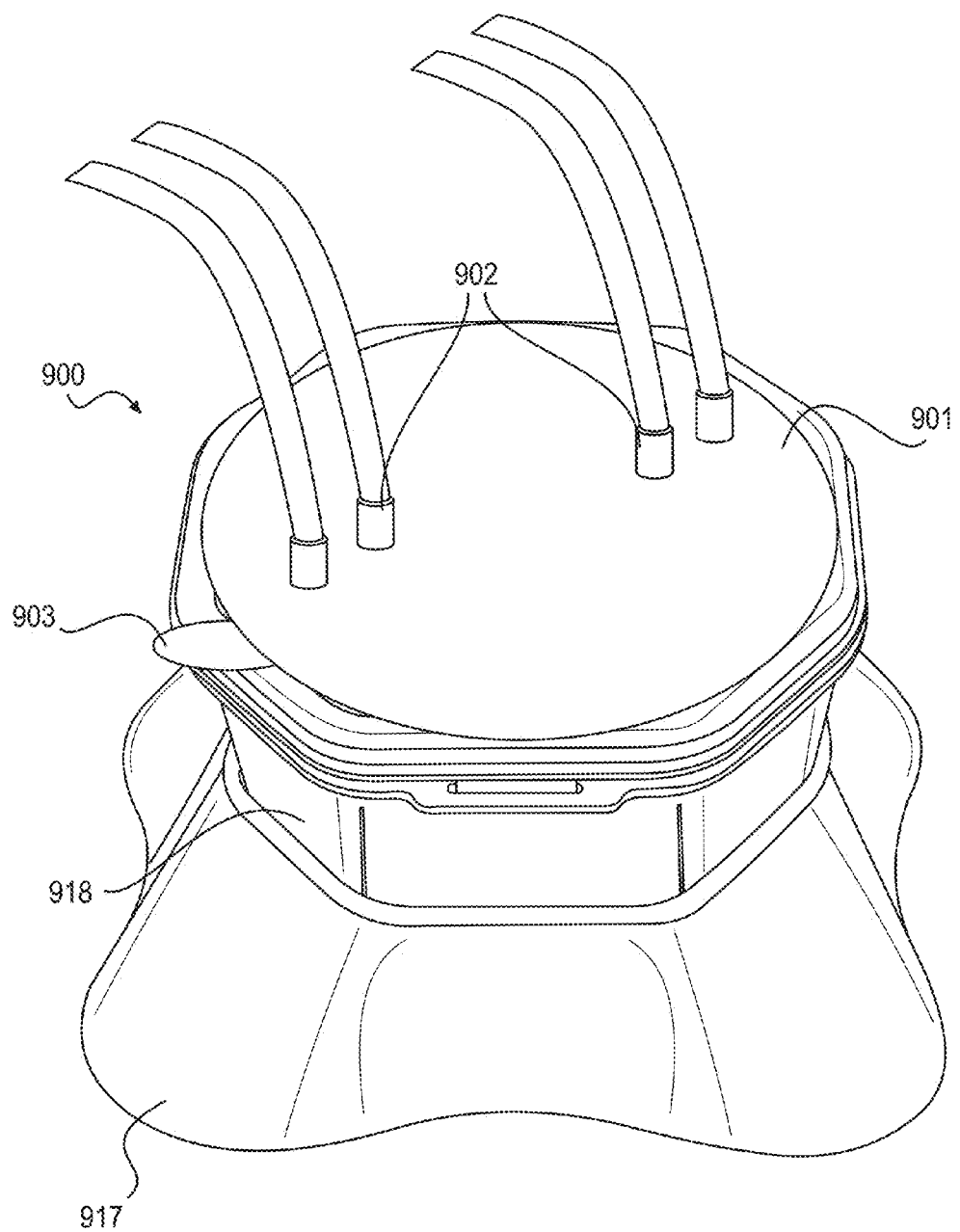
FIG. 9A illustrates a tissue processing device including a flow management device in accordance with various embodiments of the present disclosure.

FIG. 9A illustrates a tissue processing device 900 including a flow management device 901, a canister 918, and a stabilizing base 917. The flow management device 901 can include ports 902 and a handle 903, which can serve as a multi-position switch. By moving the handle 903, a user can allow, stop, or impede flow (e.g., from medical tubing) to the ports 902 and into the canister 918. In some embodiments, the canister 918 can be separated from and reattached to the stabilizing base 917.

Figure 9B:
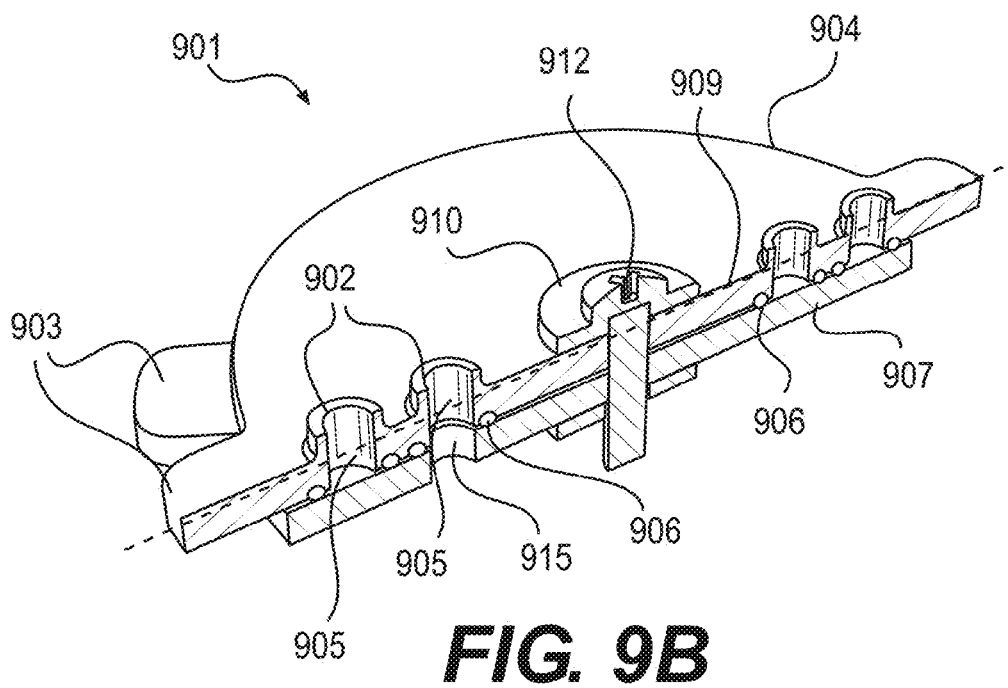
FIG. 9B illustrates a cutaway view of the flow management device of FIG. 9A in accordance with various embodiments of the present disclosure.
Figure 9C:
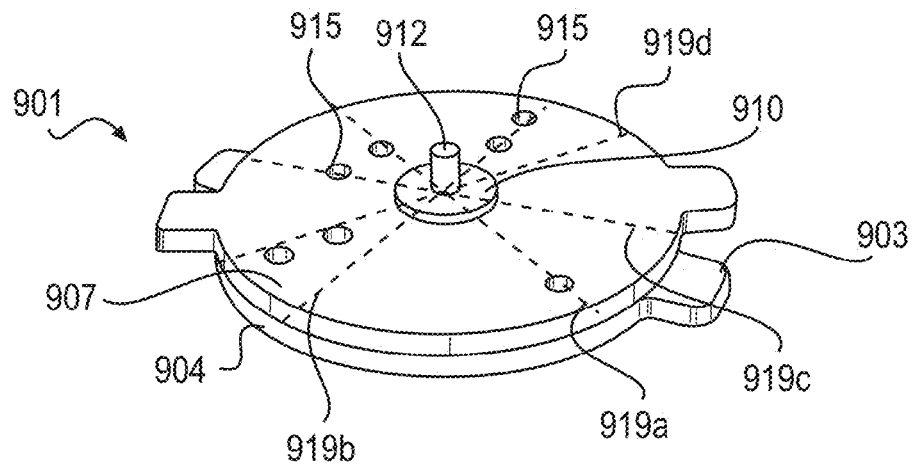
FIG. 9C illustrates a partial view of a component of the flow management device shown in FIG. 9B in accordance with some embodiments of the present disclosure.

FIG. 9B illustrates a cutaway view of the flow management device 901 of FIG. 9A while FIG. 9C illustrates a partial view of a component of the flow management device 901 in accordance with various embodiments of the present disclosure. The flow management device 901 can include a plurality of first openings 905 passing through a first plate 904 and a plurality of second openings 915 passing through a second plate 907. The first plate 904 can be placed in different rotational positions with respect to the second plate 907. In some positions of the first plate 904, a subset of the plurality of first openings 905 can be placed in fluid communication with a subset of the plurality of second openings 915 to allow passage of gases, fluids, or tissue materials through the first plate 904 and second plate 907, and therefore into or out of a treatment system.

The first plate 904 can be coupled to the second plate 907 such that the plates can be moved relative to one another to control flow through the device 901. For example, the first plate 904 and second plate 907 can be coupled using a rotatable connection such as a pivot 912 and retaining washers 910. The flow management device 901 including the first plate 904 and the second plate 907 can act as a lid to enclose the tissue processing device 900. The first plate 904 can be stationary while the second plate 907 rotates with respect to a reference (such as the canister 918). In some embodiments, the second plate 907 can be stationary while the first plate 904 rotates with respect to a reference (such as the canister 918). In some embodiments, both the first plate 904 and the second plate 907 can rotate with respect to a reference (such as the canister 918). In some embodiments, the first plate 904 and the second plate 907 can include low-friction polymers such as acetal.

Although the first and second plates are depicted in FIG. 9B as flat plates with a round perimeter, it is contemplated that the first and second plates could be any shape, dimension, or thickness that does not interfere with the purposes described herein. For example, the plurality of first openings and the plurality of second openings can be defined on curved surfaces such as walls or barriers that can translate, rotate, slide, or otherwise change position with respect to one another.

In addition, the plates can be alternatively replaced with or described as a barrier wall(s) that can prevent flow of fluid unless openings passing therethrough are aligned. Accordingly, the devices discussed herein can include a plurality of first openings 905 passing through a first barrier wall 904 and a plurality of second openings 915 passing through a second barrier wall 907. The first barrier wall 904 can be placed in different rotational positions with respect to the second barrier wall 907. In some positions of the first barrier wall 904, a subset of the plurality of first openings 905 can be placed in fluid communication with a subset of the plurality of second openings 915 to allow passage of gases, fluids, or tissue materials through the first barrier wall 904 and second barrier wall 907, and therefore into or out of a treatment system.

Figure 9D:
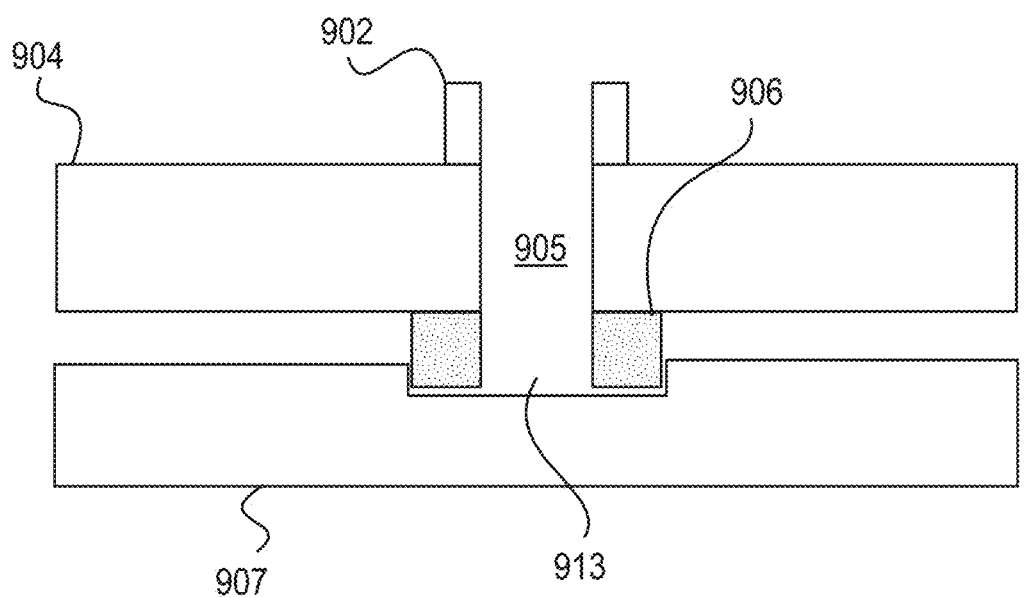
FIG. 9D illustrates a side cross-sectional view of the flow management device of FIG. 9B in accordance with some embodiments of the present disclosure.

Each of the plurality of first openings 905 or the plurality of second openings 915 can be surrounded at an end by a seal 906. The seals 906 may be an O-ring, a grommet, or any suitable sealing element. In some embodiments, the seal(s) 906 can be formed of thermoplastic elastomer (TPE) and can be molded concurrently with the first plate 904 or second plate 907 using a twin-shot molding technique. The seals 906 can create a barrier to prevent gas, fluid, or other material from escaping between the first plate 904 and the second plate 907. The first plate, second plate, or both can include a plurality of recessed portions 913 sized to fit the seals 906 as shown in FIG. 9D. The seals 906 can be placed into the recessed portions 913. When the seals 906 are placed in the recessed portion 913, the flow management device 901 is in a stored state that can avoid placing compressive forces on the seals 906 when the system is not used for an extended time such as during shipping or storage. By not subjecting the seals 906 to long periods of compression, the life of the seals 906 can be extended. In some embodiments, none of the first openings 905 is in fluid communication with any second opening 915 while the flow management device 901 is in the stored state. Although the recessed portion 906 is illustrated as being in the second plate 907 in FIG. 9D, it is also contemplated that the recessed portions 906 could be in the first plate 904 or both the first plate 904 and the second plate 907.

The first plate 904 can include ports 902 to couple tubes 912 to the first plate 904. The ports 902 can have a variety of configurations. In accordance with various embodiments, the ports 902 may be straight-walled or barbed; threaded or unthreaded; and have no fittings, luer fittings, swaged fittings, or any other type of connector suitable for a specific application. Although the ports 902 are depicted as extending out from the body of the flow management device 901, the ports may also be threaded or unthreaded holes or recesses or may extend inward from the surface into the first plate 904. Although only four ports are depicted in FIG. 9A, any number of ports can be chosen to match the number of tubes needed in a particular application. Substances including, but not limited to, gases, liquids, chemical solutions, and biological tissues can flow into or out from the ports 902 depending upon the position of the first plate or second plate and the requirements of any particular step of the medical procedure.

The flow management device 901 can include handles 903 to enable a user to more easily rotate one or both of the first plate 904 and the second plate 907. The handles 903 can be formed integrally with the first plate 904, second plate 907, or both or can be formed separately and attached.

In some embodiments, the plurality of first openings 905 can be oriented in one or more lines 909 along the first plate 904 or may be positioned in other arrangements on the first plate 904. In some embodiments, the plurality of second openings 915 can be oriented in one or more lines 919a-919d along the second plate 907, or can be positioned in other suitable arrangements on the second plate 907. Each of the lines 919a-919d can correspond, for example, to one of the steps 402, 404, 406, 408 in the decision matrix 400 as described above with reference to FIG. 4. For example, the position of the first plate 904 or second plate 907 can be adjusted to bring the line 909 including four first openings 905 into alignment with the line 919a including two second openings 915. This operation will place two first openings 905 into fluid communication with two second openings 915 as described above for step 402 in decision matrix 400. The line 909 can be aligned with other lines 919b-919d corresponding to the other steps in the decision matrix, respectively.

The flow management device 901 described above with respect to FIGS. 9A-9D includes two plates and can operate to restrict the flow by rotating the first plate 904 with respect to the second plate 907. In other embodiments taught herein below, a flow management device 1000 or system can include a third plate sandwiched between the first plate and the second plate. By changing the position or rotation of the third plate, fluid flow can be allowed or interrupted between openings in the first plate and the second plate.

Figure 10A:
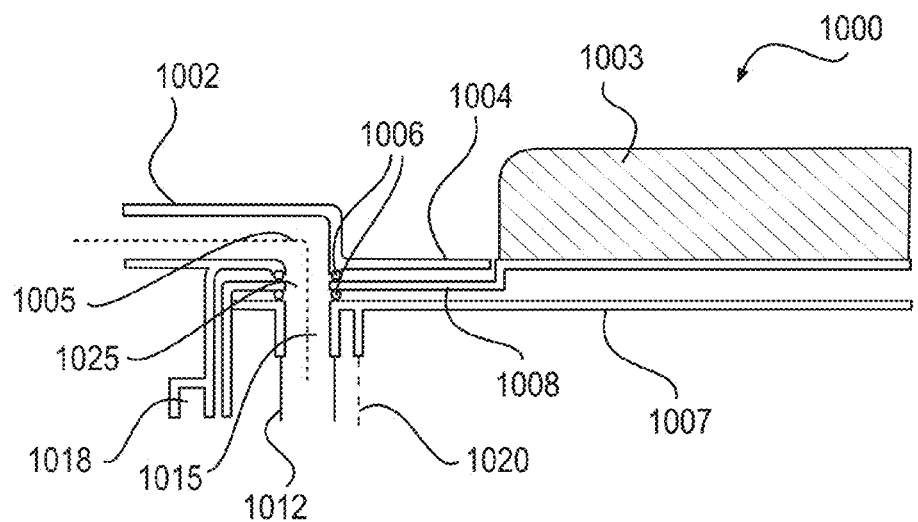
FIGS. 10A and 10B illustrate cross-sectional views of portions of flow management devices in accordance with various embodiments of the present disclosure.
Figure 10B:
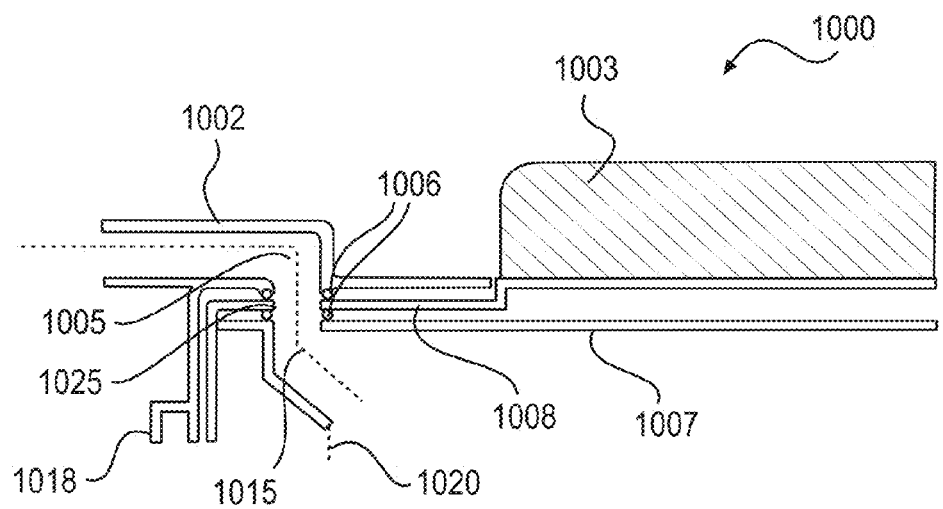

FIGS. 10A and 10B illustrate cross-sectional views of portions of flow management devices 1000 in accordance with various embodiments of the present disclosure. As shown in FIG. 10A, the flow management device 1000 includes a first plate 1004, a second plate 1007, and a third plate 1008. In some embodiments, the first plate 1004 can include a plurality of first openings 1005, the second plate 1007 can include a plurality of second openings 1015, and the third plate can include one or more third openings 1025. By placing the third plate 1008 in different rotational positions with respect to the first plate 1004 and the second plate 1007, the third openings 1025 can be configured to allow fluid communication between a subset of the first openings 1005 and a subset of the second openings 1015.

In addition, the plates can be alternatively replaced with or described as a barrier wall(s) that can prevent flow of fluid unless openings passing therethrough are aligned. Accordingly, the flow management device 1000 includes a first barrier wall 1004, a second barrier wall 1007, and a third barrier wall 1008. In some embodiments, the first barrier wall 1004 can include a plurality of first openings 1005, the second barrier wall 1007 can include a plurality of second openings 1015, and the third barrier wall can include one or more third openings 1025. By placing the third barrier wall 1008 in different rotational positions with respect to the first barrier wall 1004 and the second barrier wall 1007, the third openings 1025 can be configured to allow fluid communication between a subset of the first openings 1005 and a subset of the second openings 1015.

In accordance with various embodiments, the third plate 1008 can be disk-shaped and the one or more third openings 1025 in the third plate 1008 can be arranged at the same radial position on the disk or at different radial positions. In some embodiments, the third plate 1008 can rotate while the first plate 1004 and the second plate 1007 are stationary.

In some embodiments, the one or more third openings 1025 can be surrounded on one or both sides of the third plate 1008 by a seal 1006. In some embodiments, the seal 1006 may be an O-ring, a grommet, or any suitable sealing element. The seal 1006 can create a barrier to prevent gas, fluid, or other material from escaping between the first plate 1004 and the third plate 1008 or the second plate 1007 and the third plate 1008. In some embodiments, the first plate 1004, second plate 1007, or third plate 1008, alone or in any combination, can include a plurality of recessed portions sized to fit the seals 1006. The recessed portions can operate as described above with respect to FIG. 9D to protect the seals 1006 from experiencing extended bouts of compression. In some embodiments, none of the first openings 1005 is in fluid communication with any of the third openings 1025 disposed in the third plate 1008 or with any second opening 1015 while the flow management device 1000 is in the stored state.

In some embodiments, the first plate 1004 can include one or more ports 1002 to couple tubes 1012 to the first plate 1004 similar to the ports 902 described above with reference to FIG. 9A. Each of the one or more ports can be in fluid communication with one of the plurality of first openings 1005 in the first plate 1004. In some embodiments, the first plate 1004 can be coupled to a sidewall 1018 to form an enclosed tissue-processing device.

The multi-position switch 1003 can cause rotation of the third plate 1008 with respect to the first plate 1004 and the second plate 1007. The multi-position switch 1003 can include knobs or dials that rotate or can include handles that a user can grip to cause rotation.

In one embodiment the device can include at least two chambers separated by a filter, membrane, and/or solid wall. By aligning the various openings between the two or more plates, access to the chambers can be controlled. The chambers can be positioned next to each other in a side-by-side configuration or with one chamber on top of the other chamber. Alternatively, and as described below, a first chamber can be positioned within a second chamber.

In FIG. 10A, the combined opening formed by the first opening 1005, second opening 1015, and third opening 1025 can be used to draw a vacuum on the interior of the container 1018 using, for example, a vacuum pump or in-house vacuum provided at a facility. The vacuum can be directed into the other chamber. In accordance with various embodiments, the second plate 1007 can act as a frame to support an inner mesh 1020. The inner mesh 1020 can contain material such as tissue products while allowing fluid to pass through. In some embodiments, a transfer port can be in fluid communication with the interior volume of the container or mesh. In some embodiments, the transfer port can be in fluid communication with an inner chamber defined within the inner mesh 1020. Alternatively or additionally, the devices described herein can include additional transfer ports that are in fluid communication with the container interior outside the inner mesh 1020.

In FIG. 10B, the combined opening formed by the first opening 1005, the second opening 1015, and the third opening 1025 can be used to transport fluids such as Ringer's solution or tissues such as those associated with liposuction (i.e., liposuction-derived adipose tissue). In some embodiments, the second opening 1015 can be connected to an inner chamber such that tissue products entering through the second opening 1015 are captured inside the inner chamber. In some embodiments, the second opening 1015 can be connected to an outer chamber such that fluids in the outer chamber can be removed through the second opening 1015.

As shown in FIGS. 10A and 10B, a portion of the second opening can define a pathway that directs flow of fluids, gasses, and/or solids into the inner and/or outer chamber. As shown in FIG. 10B, the second opening can define a pathway inside the device that directs material into a desired location within the device. In one embodiment, the second opening has an angled configuration to direct material into the inner chamber of the device. As shown in FIG. 10B, vacuum tubing 1012 can be coupled to the second plate 1007 to extend a pathway into a desired location within the device.

Figure 11A:
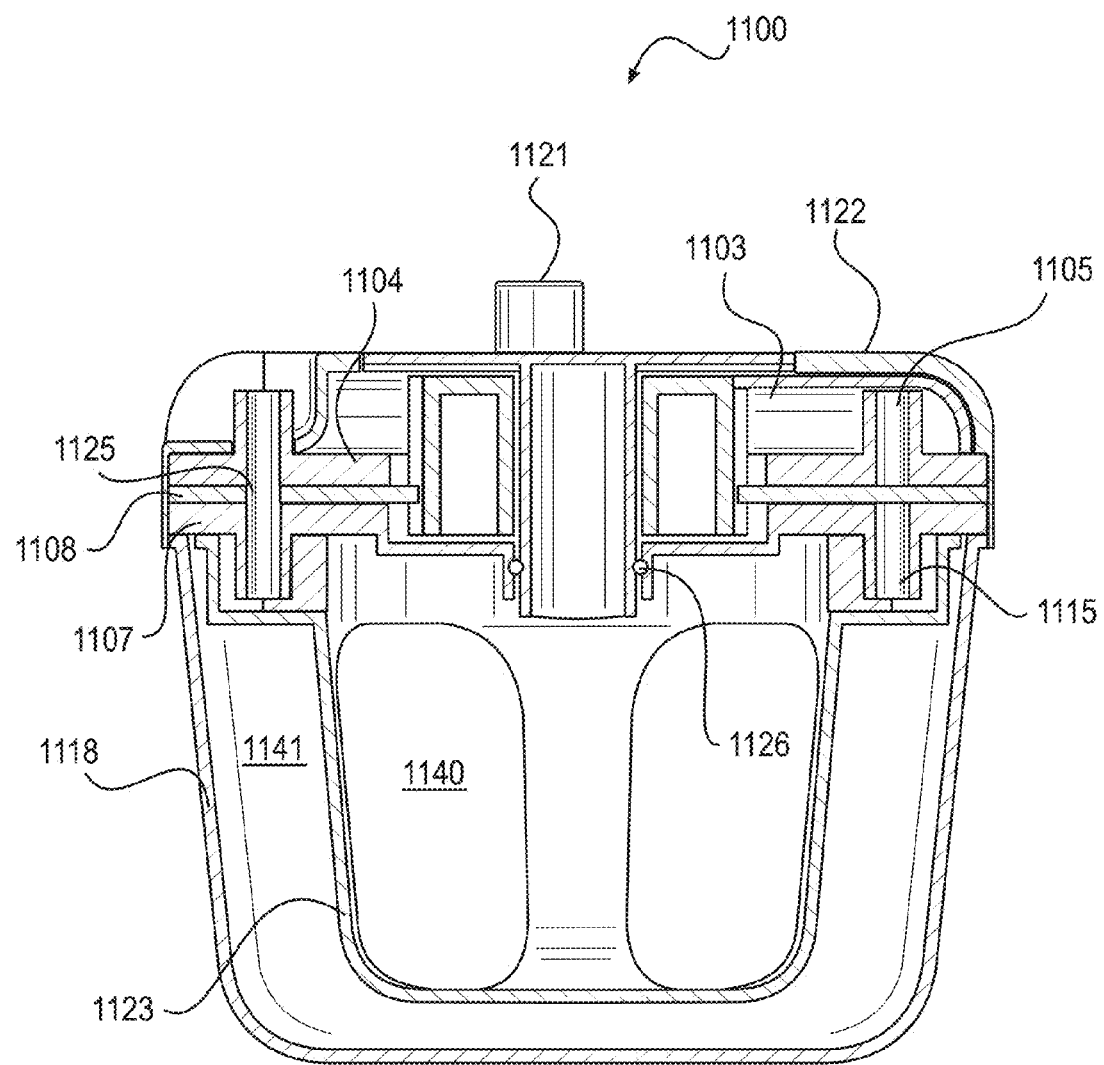
FIG. 11A illustrates a cutaway view of a tissue treatment system including an integrated flow management device in accordance with various embodiments of the present disclosure.
Figure 11B:
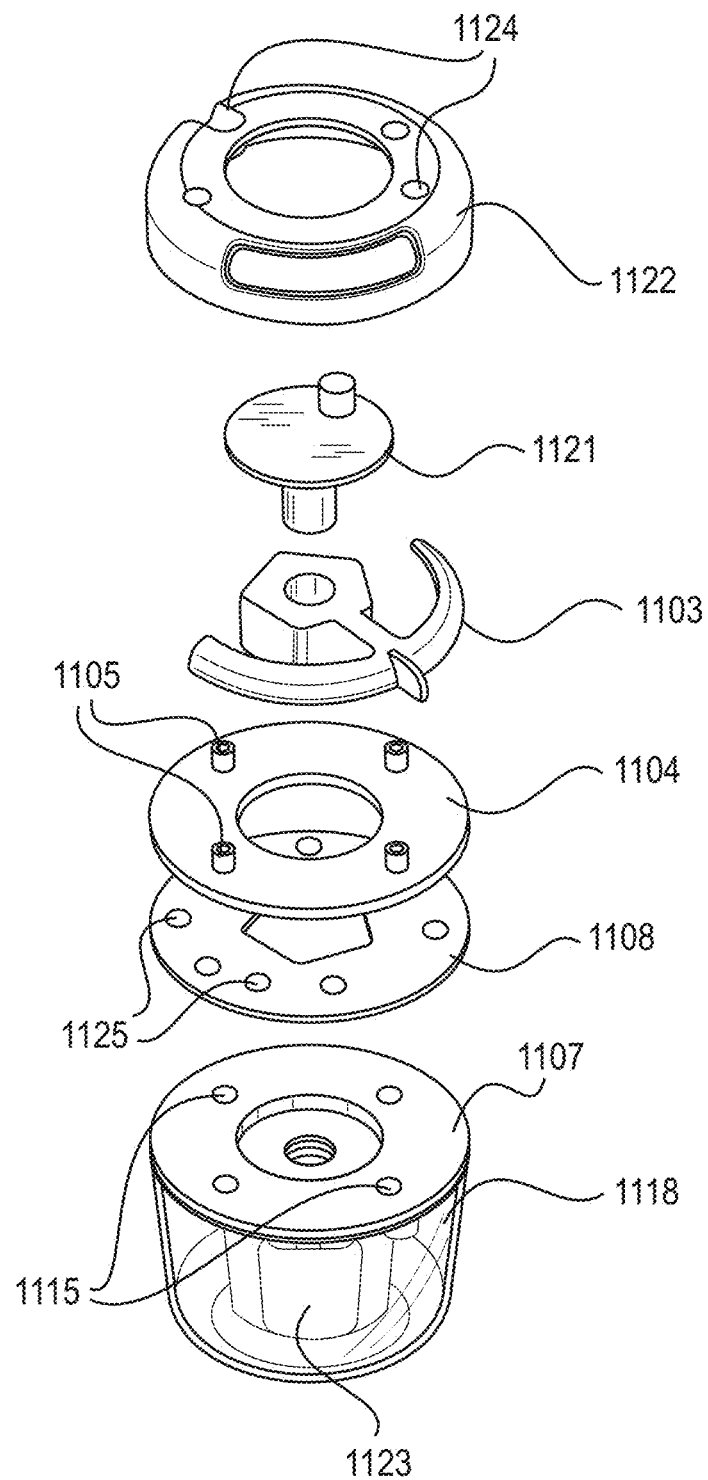
FIG. 11B illustrates an exploded view of the tissue treatment system of FIG. 11A.

FIGS. 11A and 11B illustrate a cutaway view and an exploded view, respectively, of a tissue treatment system 1100 including an integrated flow management device in accordance with some embodiments of the present disclosure. The flow management device is similar to the flow management device 1000 described above with respect to FIGS. 10A or 10B. The tissue treatment system 1100 can include a top cover 1122, a rotary handle 1121, a multi-position switch 1103, a first plate 1104 including a plurality of first openings 1105 therethrough, a second plate 1107 including a plurality of second openings 1115 therethrough, a third plate 1108 including one or more third openings 1125 therethrough, a container 1118, and a filter 1123. When assembled, the tissue treatment system 1100 can be used in some embodiments to process adipose tissue including steps such as aspiration, irrigation, mixing, separation, or transfer. By operating the multi-position switch 1103 coupled to the third plate 1108, the third openings 1125 can be positioned to allow fluid communication between a subset of the first openings 1105 and a subset of the second openings 1115. In some embodiments, placement of the multi-position switch 1103 in a first position can connect a subset of first openings 1105 to a subset of second openings 1115 that are in fluid communication with the inner chamber 1140 of the system 1100. In some embodiments, placement of the multi-position switch 1103 in a second position can connect a subset of first openings 1105 to a subset of second openings 1115 that are in fluid communication with the outer chamber 1141 of the system 1100.

In some embodiments, the top cover 1122 can be attached to the container 1118 using a snap fit or an adhesive to promote sterility inside the tissue treatment system 1100. In some embodiments, the top cover 1122 can include openings or recesses 1124 to connect the first openings 1105 to the exterior of the device. In some embodiments, the top cover 1122 can fit over or sandwich the multi-position switch 1103.

After cleaning the tissue within the device, it can be important not to allow inadvertent access to the clean tissue to avoid contamination and to maintain sterile conditions within the device. In some embodiments, the second plate 1107 can be permanently affixed to the container 1118. By affixing the second plate 1107 to the container 1118, a seal can be formed that prevents contamination from entering the device. In some embodiments, the second plate 1107 can be affixed to the container 1118 using adhesives, heat sealing, or fasteners such as screws.

In accordance with various embodiments, the third plate 1108 can be disk-shaped and the one or more third openings 1125 in the third plate can be arranged at the same radial position on the disk or at different radial positions. In some embodiments, the third plate 1108 can rotate while the first plate 1104 and the second plate 1107 are stationary. In some embodiments, the first plate 1104 and second plate 1107 are coupled to sandwich or retain the third plate 1108 between them. As discussed above with reference to FIG. 10A, the one or more third openings 1125 can be surrounded on one or both sides of the third plate 1108 by a seal.

The rotary handle 1121 can extend through the center of the tissue treatment system 1100 and engage with mixing blades (not shown) in the filter 1123 or container 1118. By rotating the rotary handle 1121, tissue within the filter 1123 or container 1118 can be mechanically processed to allow washing or separation of components of the tissue as part of a tissue treatment regimen. In some embodiments, the filter 1123 can be a filter structure as described in greater detail below with reference to FIGS. 16A-18B. In an exemplary embodiment, the filter 1123 can act as a dividing wall or barrier to separate an inner chamber 1140 from an outer chamber 1141.

In some embodiments, the first plate 1104 can include one or more ports to couple tubes to the first openings 1105 of the first plate 1104 similar to the ports 902 described above with reference to FIG. 9A. In some embodiments, the rotary handle 1121 can engage with a seal 1126 that prevents fluids, gases, or tissue components from exiting the filter 1121 or container 1118. In accordance with various embodiments, the seal 1126 can be integrated into the rotary handle 1121 or into the second plate 1107.

The multi-position switch 1103 can cause rotation of the third plate 1108 with respect to the first plate 1104 and the second plate 1107 in some embodiments. The multi-position switch 1103 can include knobs or dials that rotate or can include handles that a user can grip to cause rotation. In some embodiments, a portion of the multi-position switch 1103 can have a complementary shape to a central hole of the third plate 1108. For example, the central hole of the third plate 1108 can be shaped as a pentagon or other polygonal shape and the portion of the multi-position switch 1103 can be shaped as a pentagon that fits within the hole of the third plate 1108. The complementary shapes of the portion of the multi-position switch 1103 and the central hole of the third plate 1108 can enable the multi-position switch 1103 to engage and rotate the third plate 1108 in some embodiments.

In some embodiments, the second plate 1107 can be coupled to the container 1118 using a snap fit or adhesive fit.

Figure 12A:
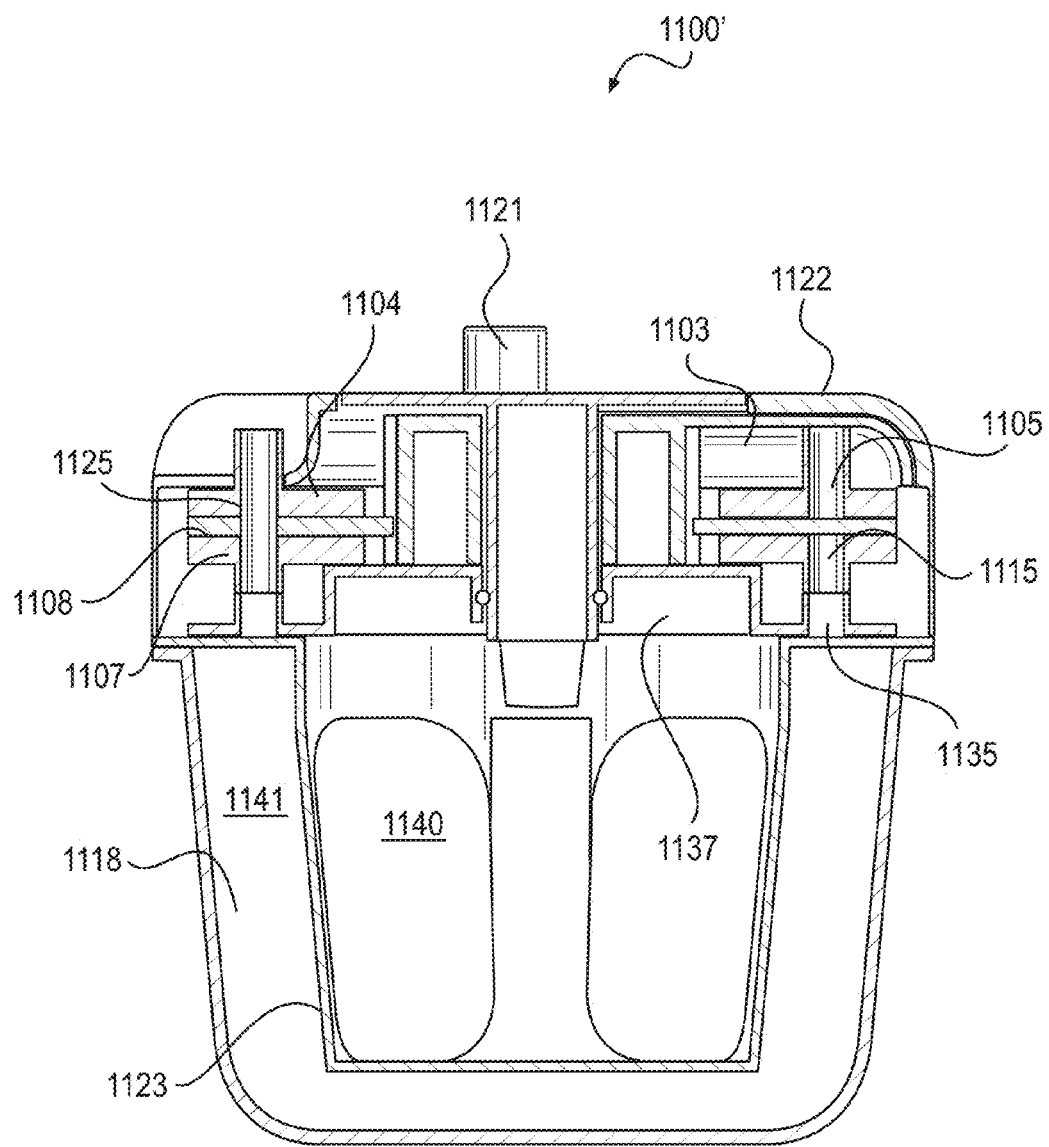
FIG. 12A illustrates a cutaway view of a tissue treatment system including a flow management device subassembly in accordance with various embodiments of the present disclosure.
Figure 12B:
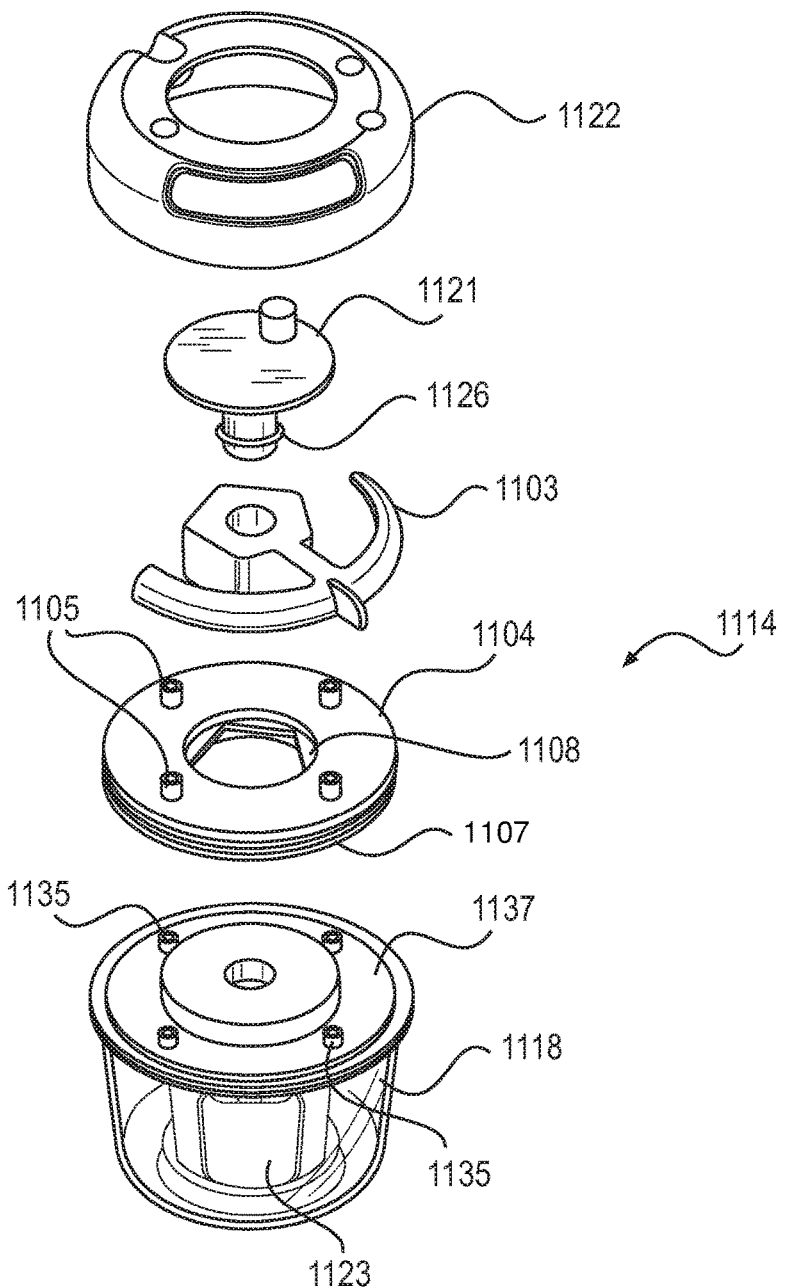
FIG. 12B illustrates an exploded view of the tissue treatment system of FIG. 12A.

FIGS. 12A and 12B show a cutaway view and an exploded view, respectively, of an alternative embodiment of a tissue treatment system 1100' including an integrated flow management device. The flow management device is similar to the flow management device described above with respect to FIGS. 10A or 10B. The primary difference between the tissue treatment system 1100 of FIGS. 11A-11B and the tissue treatment system 1100' of FIGS. 12A and 12B relates to component integration and manufacturing. The tissue treatment system 1100' can include a valve assembly 1114 that includes the first plate 1103, the second plate 1107, and the third plate 1108. The tissue treatment system 1100' can also include a filter top 1137 that includes a plurality of third openings 1125 that connect the interior of the container 1118 and the second openings 1115 of the second plate 1107. By operating the multi-position switch 1103 coupled to the third plate 1108, the third openings 1125 can be positioned to allow fluid communication between a subset of the first openings 1105 and a subset of the second openings 1115 thereby also placing a subset of the third openings 1125 in fluid communication with the subset of the first openings 1105.

After cleaning the tissue within the device, it can be important not to allow inadvertent access to the clean tissue to avoid contamination and to maintain sterile conditions within the device. In some embodiments, the filter top 1137, top cover 1122, or both can be permanently affixed to the container 1118. By affixing the filter top 1137 and the container 1118, a seal can be formed that prevents contamination from entering the device. In some embodiments, the filter top 1137, top cover 1122, or both can be affixed to the container 1118 using adhesives, heat sealing, or fasteners such as screws.

The filter top 1137 can be coupled with the filter 1123 using a snap fit or an adhesive fit. In some embodiments, the filter assembly 1114 can be replaceable or interchangeable. In some embodiments, the tissue treatment device 1100' can be provided with multiple filter assemblies 1114 that are configured to correspond to different sets of tissue treatment protocols. In such embodiments, the user can select a filter assembly 1114 to fit their application at the beginning of the procedure and can snap the filter assembly 1114, multi-position switch 1103, rotary handle 1121, and top cover 1122 in place.

Embodiments described above include one or more walls or barriers such as flat plates to restrict or allow flow between the first openings and the second openings. In alternative embodiments described below with respect to FIGS. 13A-14B, different components such as cylindrical spindles or diaphragm values provide the capability to restrict flow between first and second openings.

Figures 13A, 13B:
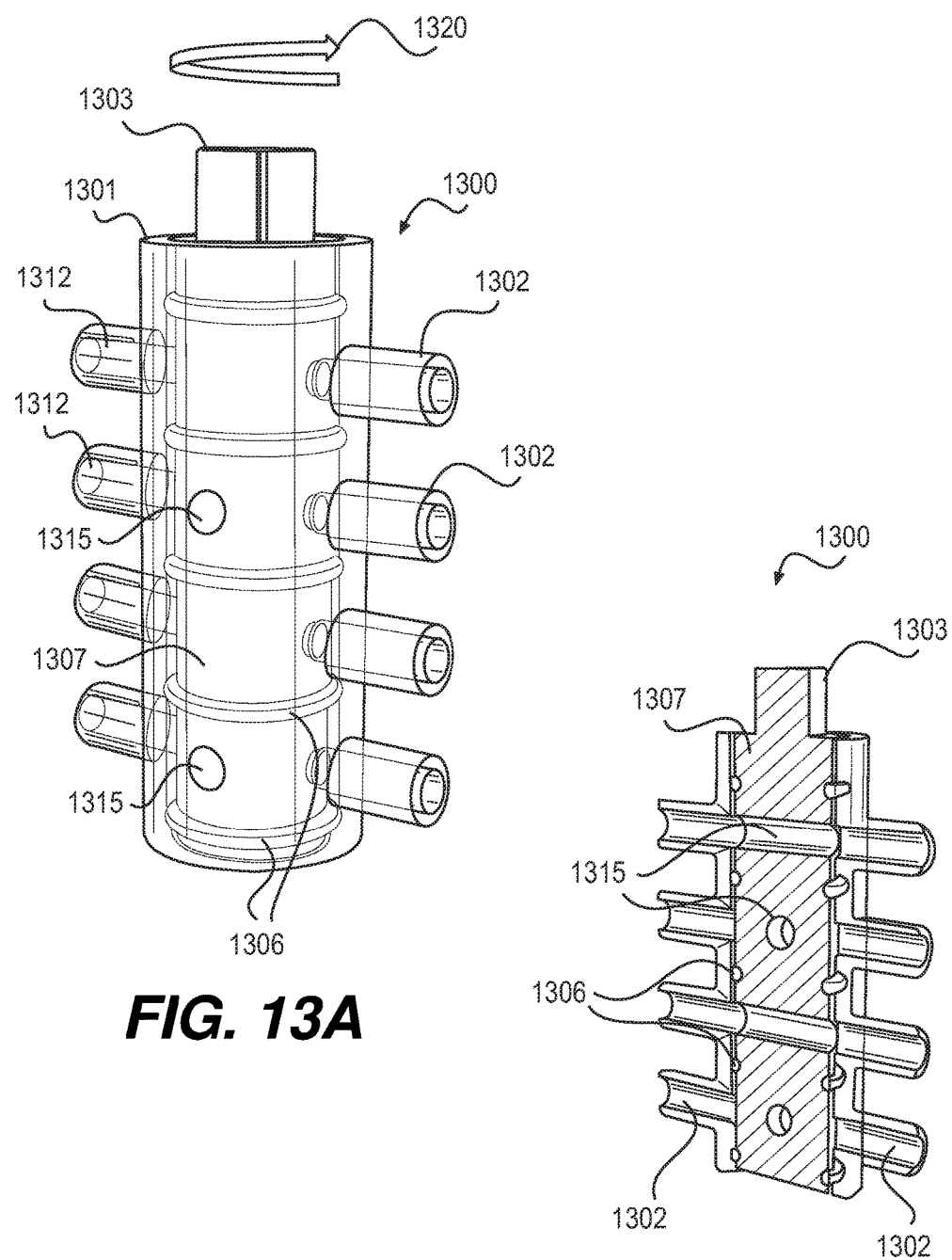
FIG. 13A illustrates a flow management device including a spindle in accordance with various embodiments of the present disclosure.
FIG. 13B illustrates a cross-sectional view of the flow management device shown in FIG. 13A.

FIG. 13A depicts a flow management device 1300 including a spindle in accordance with various embodiments of the present disclosure. FIG. 13B illustrates a cross-sectional view of the flow management device 1300. The flow management device 1300 includes a body 1301 having a plurality of first openings 1302 and a plurality of second openings 1312, a spindle 1307 coupled to a multi-position switch 1303 and a plurality of third openings 1315. By operating the multi-position switch 1303, the spindle 1307 can rotate in a direction 1320. Operation of the multi-position switch 1303 can position some or all of the third openings 1315 to place a subset of the first openings 1302 into fluid communication with a subset of the second openings 1312.

In some embodiments, the plurality of third openings 1315 can include more than one opening each axial position of the spindle 1307. In such embodiments, different openings at the same axial position can have different azimuthal trajectories. The use of multiple openings at the same axial position along the spindle 1307 can increase the number of possible connection configurations for a given spindle 1307. According to the rotational orientation of the spindle 1307, each of the third openings 1315 can connect one of the first openings 1302 to one of the second openings 1312.

In some embodiments, seals 1306 may be placed at positions along the spindle 1307 to obstruct the passage of fluid, gas, or tissue material between the spindle 1307 and the body 1301. The seals 1306 can be O-rings, grommets, or gaskets and can be made of rubber, polymer, or any other suitable material. In some embodiments, the seals 1306 can be formed of thermoplastic elastomer using a molding technique such as twin-shot molding.

The multi-position switch 1303 can be integrated directly into the spindle 1307 in some embodiments or can be a separate device that causes the spindle 1307 to rotate. In some embodiments, the multi-position switch 1303 can be operated by hand. In some embodiments, the multi-position switch 1303 can be optimally shaped to enable the use of tools such as wrenches to improve a user's leverage in setting the multi-position switch 1303. Although the multi-position switch 1303 is shown rotating in direction 1320 in FIG. 13A, the multi-position switch 1303 can be rotated in either direction in some embodiments.

The body 1301 can include ports or connections adjacent to the first openings 1305 or the second openings 1315 that allow connection to a variety of different tubes or hoses. For example, the ports or connections adjacent to the first openings 1305 or the second openings 1315 can include barbs, threads, fittings or other appropriate connectors.

Figure 14A:
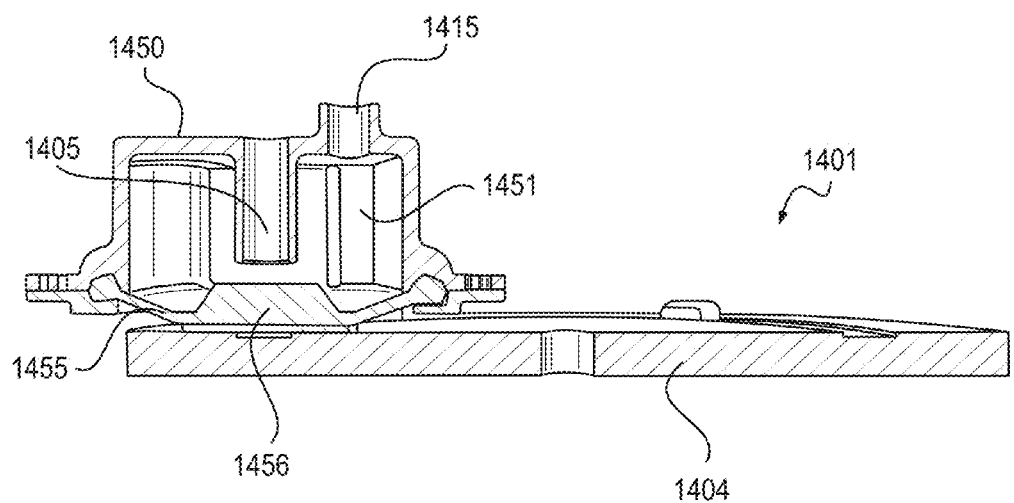
FIG. 14A illustrates a cross-sectional view of a flow management device including a diaphragm valve in an open position in accordance with various embodiments of the present disclosure.
Figure 14B:
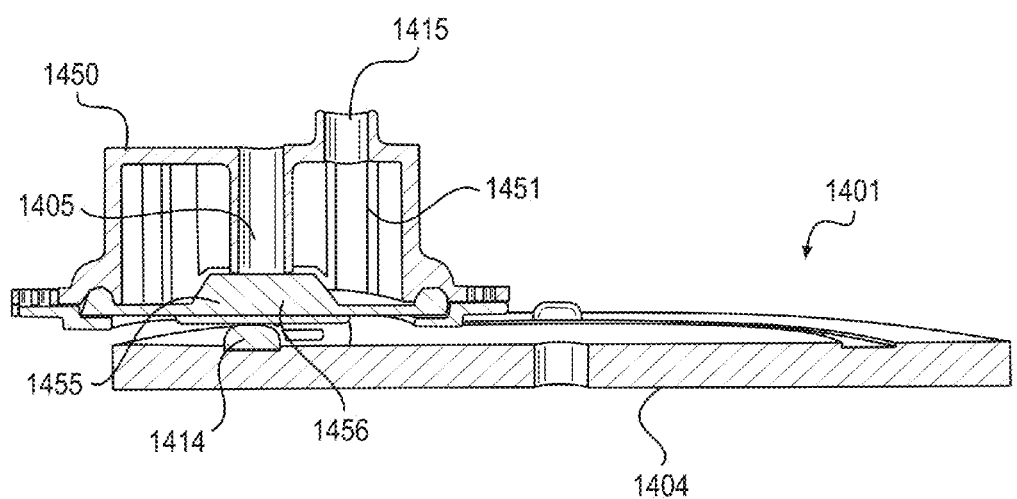
FIG. 14B illustrates a cross-sectional view of the flow management device including a diaphragm valve in a closed position in accordance with various embodiments of the present disclosure.

FIGS. 14A and 14B illustrate a flow management device 1401 including a diaphragm valve in open and closed positions, respectively, according to various embodiments of the present disclosure. The flow management device 1401 can include a rotating plate 1404, and one or more diaphragm units 1450. The diaphragm unit 1450 can include a flexible diaphragm 1455 and an inner chamber 1451. The flexible diaphragm 1455 can be actuated to open or close fluid pathways in the flow management device 1401. In some embodiments, the diaphragm 1450 can include materials such as silicone. In some embodiments, the diaphragm 1455 can include a boss 1456.

In an open position, the diaphragm unit 1450 places a first opening 1405, inner chamber 1451, and second opening 1415 into fluid communication. In a closed position, the first opening 1405 of the diaphragm unit 1450 is no longer in fluid communication with the inner chamber 1451 or the second opening 1415.

The rotating plate 1404 can include one or more protrusions 1414. In some embodiments, the rotating plate 1404 can be rotated to different rotational positions with respect to the diaphragm units 1450. By rotating the rotating plate 1404, a protrusion 1414 can be positioned below the diaphragm unit 1450. The protrusion can force the flexible diaphragm 1455 upwards to seal the boss 1456 against the one or more first openings 1405 passing through the diaphragm unit 1450 thereby placing the diaphragm unit 1450 in a closed position. By sealing the one or more first openings 1405, the diaphragm 1450 can interrupt fluid communication between the first openings 1405 and second openings 1415.

In some embodiments, a separate diaphragm unit 1450 can be supplied for each fluid connection that is to be controlled. In some embodiments, a single diaphragm unit can include more than one boss 1456, more than one first openings 1405, or more than one second openings 1415. In some embodiments, rotating plate 1404 can have small patterns of protrusions 1414 at different azimuthal positions on the plate 1404 to simultaneously provide control of multiple diaphragm units 1450 for each position of the rotating plate 1404.

In FIG. 15A, a tissue treatment system 1530 is illustrated that includes a turbine 1520 in accordance with various embodiments. The turbine 1520 can turn the mixing shaft 1535 including mixing blades or paddles 1534 to agitate the tissue inside the tissue treatment system. The turbine 1520 can include a rotor with a central shaft 1521 and rotor blades 1528 as shown in FIG. 15C. In some embodiments, the turbine 1520 can have an air intake 1522 and air outlet 1525. Upon attachment of the air outlet 1525 to a source of negative pressure such as a vacuum pump, the rotor blades 1528 will move thus turning the central shaft 1521.

As shown in FIG. 15B, the end 1526 of the central shaft 1521 can engage with the mixing shaft 1535 so that the central shaft 1521 and mixing shaft 1535 rotate in concert. In accordance with various embodiments, the engagement of the central shaft 1521 with the mixing shaft 1535 can take any suitable form. For example, as shown in FIG. 15B, the end 1526 of the central shaft 1521 can have a hexagonal cutout that matches a hexagonal extension on the mixing shaft 1535. Other shapes are also possible including squares, stars, and other polygons. In some embodiments, the turbine 1520 can be separated from the base of the tissue treatment system 1530, and a manually operated rotation system such as a rotary handle can be installed in its place. In some embodiments, the separable turbine 1520 can be sterilizable or reusable to allow use of a single turbine 1520 for multiple tissue processing procedures with multiple tissue treatment canisters or containers. In some embodiments, the turbine 1520 can be disposable.

Because a solution including washing fluids and adipose or other tissues can be viscous, a user that is manually agitating the tissue may become fatigued before the washing sequence is complete. In addition, the agitation may be inconsistent if the user varies the speed of rotation of the rotary handle throughout the washing sequence. Rotation of the mixing shaft 1535 using a turbine 1520 can improve consistency of mixing. For example, a constant level of negative pressure applied at the air outlet 1525 can cause the mixing shaft 1535 to rotate at a constant rate of rotation. In addition, the turbine 1520 can operate at a consistent speed for an extended period of time as necessary according to the needs of the practitioner.

Figure 15D:
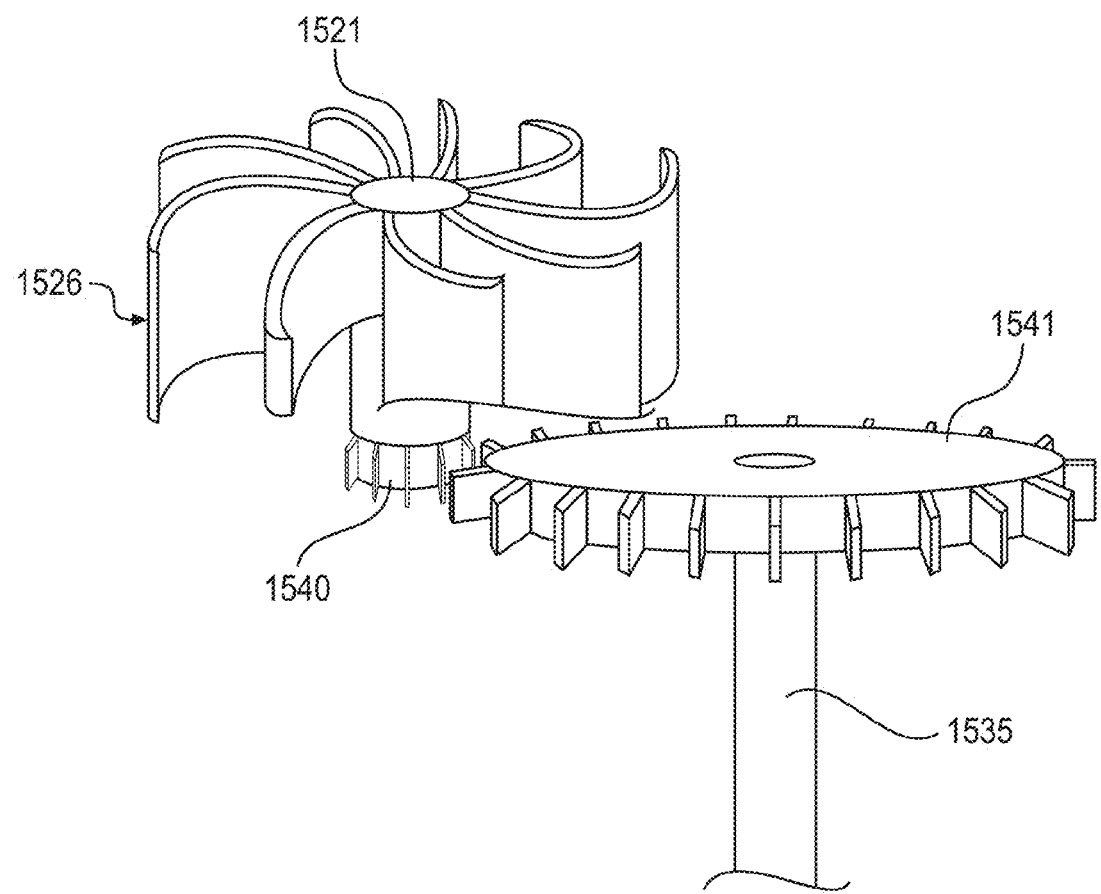
FIG. 15D illustrates engagement of a turbine with a mixing shaft through a gear system in accordance with various embodiments of the present disclosure.

FIG. 15D illustrates a modification to the turbine wherein a smaller gear 1540 is attached to the central shaft 1521. The teeth of the smaller gear 1540 can engage with teeth on a larger gear 1541 attached to the mixing shaft 1535. In some embodiments, the ratio of sizes of the smaller gear 1540 and the larger gear 1541 can be chosen to optimize rotations per minute of the mixing shaft 1535 for adipose tissue washing. In some embodiments, the tissue treatment system 1530 can include multiple removable and attachable small gears 1540 or large gears 1541 to enable a practitioner to tune the gear ratio and, thus, the speed of rotation to the desired level.

Figure 16B:
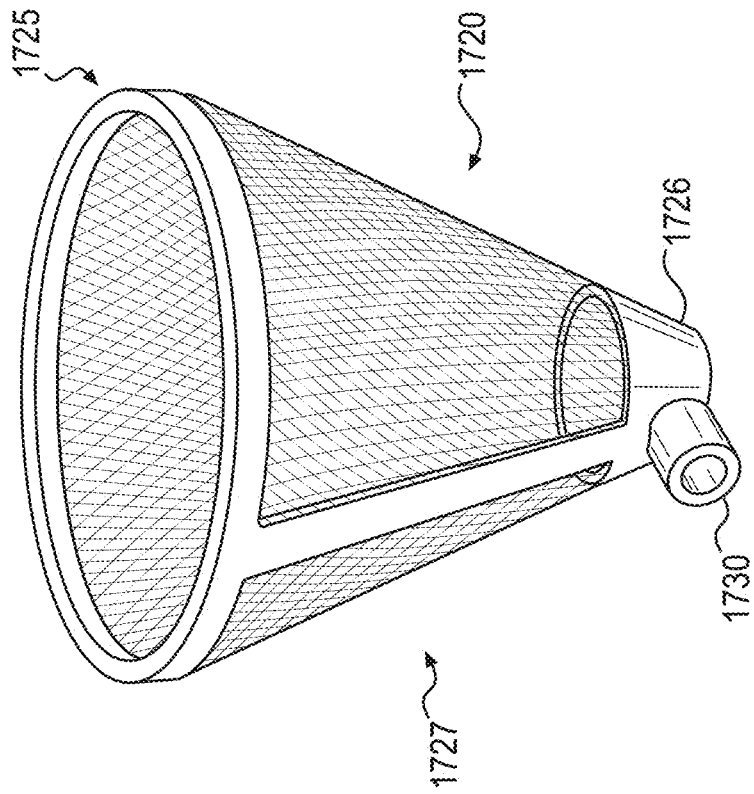
FIGS. 16A and 16B illustrate various mesh filters for use in tissue treatment systems according to various embodiments of the present disclosure.
Figure 16A:
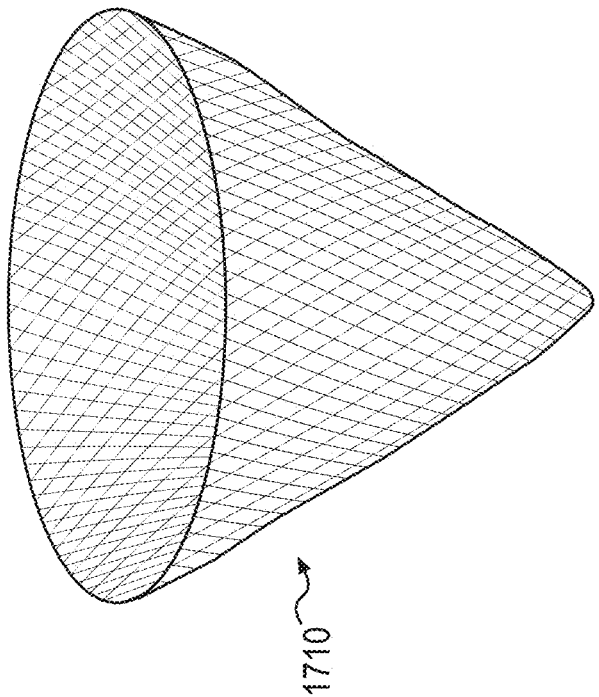

FIGS. 16A and 16B illustrate one embodiment of a filter structure that can divide first and second portions or chambers of the devices and systems described herein. The dividing wall defined by the filter structure can include a frame member 1725 that provides structural support. Frame member 1725 can be formed of a material that provides rigidity and is formed from solid material. In one aspect, the frame member 1725 is formed of liquid-impervious material. Frame member 1725 can mate with or be formed integral with a top portion of the device. For example, the frame member 1725 can mate with or be formed integral to a second plate 1107 as described above with reference to FIG. 11A. The bottom portion 1726 of the frame member 1725 can define a transfer port 1730 for removal of materials from within the inner chamber of the device adjacent to the bottom portion of the device. In one aspect, frame member 1725 extends from the top portion of the interior of the device to the bottom of the interior of the device. In some embodiments, the frame member 1725 can surround an upper border of the filter 1710 or mesh wall. In additional embodiments, the frame member 1725 can extend along at least a portion of a side wall of the mesh wall to a bottom portion of the mesh wall.

Frame member 1725 can include a window 1727 defined by the frame member. Various filters 1710 can be mated with the frame member to allow movement of liquid and gas from between the inner and outer chambers of the device. The filter 1710 can be mated within one or more windows 1727. For example, as shown in FIG. 16B, a window defined between the top and bottom portions of the frame member can include a filter 1710. The filter 1710 can define a portion of the dividing wall that divides the first and second chambers of the device. In one embodiment, the filter and/or filter windows do not extend to the top most part and/or bottom most part of the frame member. Alternatively, a single filter 1710 can be seated within the frame member. In some embodiments, the filter 1710 can be a mesh wall supported by the frame or frame member that acts to divide the first chamber from the second chamber.

In some embodiments, a mesh filter 1710 as shown in FIG. 16A can have a conical shape. In various embodiments, the narrow end of the mesh filter 1710 can come to a point or a line seam, or the mesh filter 1710 can have a flat panel on the bottom. In some embodiments, the cone shape of the mesh filter 1710 can smooth out areas where adipose tissue or other tissue components can get stuck. As shown in FIG. 16B, a mesh filter 1720 can also include a superstructure 1725 to provide greater form and stability to the mesh filter 1720. In some embodiments, the superstructure 1725 can be overmolded plastic. In some embodiments, the mesh filter 1720 can include an integrated transfer port 1730. The transfer port 1730 can be used to extract tissue from a tissue treatment system after washing, separating, and mixing cycles are complete.

FIGS. 17A and 17B illustrate a disassembled and assembled filter structure 1810, respectively, according to various embodiments of the present disclosure. The filter structure 1810 can include a frame member 1850 and a filter 1815. The frame member 1850 can include one or more windows 1827. In some embodiments, the filter 1815 can be mated within the windows 1827.

In some embodiments, the filter 1815 can include cut-through holes 1816 to hold the filter in place against the frame member 1850. In some embodiments, the frame member 1850 can include a boss feature 1856 or other catch feature to engage with the cut-through holes 1816 and position the filter 1815. In accordance with various embodiments, the filter 1815 can be cut to fit the frame member 1850 such that removed portions 1818 of the filter 1815 line up with solid portions 1858 of the frame member 1850. In some embodiments, the solid portions 1858 comprise extensions from the frame member 1850. The frame member 1850 can surround an upper border of the filter 1815 and have multiple solid portions 1858 as extensions along at least a portion of a side wall of the mesh wall to a bottom portion of the mesh wall. In accordance with various embodiments, the filter 1815 can include a synthetic or natural mesh-like material.

The filter structure 1810 can include a transfer port 1860 near the bottom of the filter structure. In prior systems, removal of cleaned tissue from the tissue treatment system generally required inversion of the tissue treatment system to bring the tissue in proximity to an entry/exit port at the top of the device. In this case, inversion of the device is undesirable as it requires the device to be completely disconnected from attached tubing and awkwardly held upside-down by a practitioner. Alternatively, a separate port having an extension tube was used to extract clean tissue from the device. In this case, the tube typically presented an obstruction to the motion of the mixing blades, and tissue trapped near the tube did not properly wash or mix. In embodiments of the present disclosure, the transfer port 1860 can allow removal of tissue from the tissue treatment system through or near the bottom of the container. The tissue can be drawn into the transfer port 1860 by gravity or through the application of negative pressure. In some embodiments, the transfer port 1860 can be used to extract fluids, gases, or solids or can be used to insert fluids, gases, or solids. In certain embodiments, the transfer port 1860 can be in fluid communication with the inner chamber of a tissue treatment device as described above with reference to FIGS. 11A and 12A. In other embodiments, the transfer port 1860 can be in fluid communication with the outer chamber of the tissue treatment device. In some embodiments, a portion of the transfer port 1860 can be equipped to engage with syringes of various sizes, luer locks, or any other suitable connector 1861.

FIG. 17C illustrates a tissue treatment system 1800 including a filter structure 1810 in accordance with various embodiments described herein. The tissue treatment system 1800 can include a plurality of ports 1802, one or more mixing blades 1830, a base 1870, and a filter structure 1810.

As described above with reference to FIGS. 17A-17B, the filter structure can divide first and second portions or chambers of the tissue treatment system 1800. The dividing wall defined by the filter structure 1810 can include a frame member 1850 that provides structural support. In various embodiments, frame member 1850 can mate with or be formed integral with a top portion of the device. For example, the frame member 1850 can mate with or be formed integral to a second plate 1107 as described above with reference to FIG. 11A. In some embodiments, the filter structure, top portion, and bottom portion of the device including a transfer port 1860 can be built into one interior wall of the device. The bottom portion of the frame member 1850 can define a transfer port 1860 for removal of materials from within the inner chamber of the device adjacent to the bottom portion of the device. In one aspect, frame member 1850 extends from the top portion of the interior of the device to the bottom of the interior of the device. In some embodiments, the frame member 1850 can surround an upper border of the filter 1815 or mesh wall. In additional embodiments, the frame member 1850 can extend along at least a portion of a side wall of the mesh wall to a bottom portion of the mesh wall.

The manual forces that are applied to operate the handle 1804 to properly mix and wash tissue using the mixing blade(s) 1830 may be significant for some forms of tissue. In a typical setup, tissue washing and mixing will occur after other steps in a surgical procedure have already been performed such as tissue extraction. Mid-operation, the examination gloves worn by the surgeon or practitioner may contain foreign matter or fluid of a slippery nature that can make it difficult to grasp and operate the handle without tipping over the device. In accordance with various embodiments, the tissue treatment system 1800 can include a wide base 1870 (or 917 in FIG. 9A) at the bottom of the system to improve stability and prevent tipping or movement of the device during tissue mixing and washing. In some embodiments, the underside of at least a portion of the wide base 1870, 917 can include a high-friction, textured, or tacky substance such as rubber to prevent slipping or skidding of the tissue treatment system 1800 during use. In some embodiments, the wide base 1870, 917 can include fluids, metals, or other high density materials to provide additional weight to the base.

The wide base is illustrated with a couple of specific configurations, but it should be understood that the base can be modified to accomplish any one or more of maintaining device stability and preventing accidental tipping or movement. The base can include a flared outward section or other configurations (e.g., a box, a series of extensions, or multiple legs). The base can be defined by a widened section, for example, having a footprint or widest dimension that is 10%, 20%, 30%, 40% or more greater than the widest dimension of the lowest portion of the container of the treatment system, or 10%, 20%, 30%, 40% or more greater than the widest dimension of the top of the treatment system (thereby preventing a top-heavy or unstable structure).

In some embodiments, the tissue treatment device 1800 can include a multi-position switch 1806. The multi-position switch can operate to place different subsets of first openings in fluid communication with subsets of second openings as described above with reference to FIGS. 9A-12B.

FIG. 18A illustrates an exploded view of a conical filter structure 1910 for use in tissue treatment systems according to various embodiments of the present disclosure. Although illustrated in conjunction with a particular treatment system, the filter structure can be incorporated with any of the aforementioned tissue treatment systems described herein. As discussed further below, the filter structure can include a filtering portion or mesh structure that allows flow of fluid or debris of a selected size, while retaining tissue to be treated and/or implanted. In addition, the structure includes a frame, which can include a rigid, semi-rigid, or otherwise strong material to support the structure. The frame and filtering portion or mesh, together provide important advantages.

For example, known filters, such as polymeric meshes, may be prone to breakage, especially with vigorous washing or transfer processes. Accordingly, the frame, in its various possible configurations, allows a more robust structure that is less prone to failure during surgical processing. In addition, the filter can extend towards or all the way to the bottom of the treatment system. The extension to the bottom of the treatment system can allow formation of supporting side walls in the frame, and can allow further support of the filter by the bottom wall of the system. In addition, the filter, by extending toward the bottom of the system and including a frame, which itself can extend to and form a bottom portion of the filter, can be configured to engage with one or more transfer ports, thereby allowing insertion and/or extraction of fluids and tissue from the system's bottom—thereby obviating the need for top-only access using syringes or other devices.

Specific details of an exemplary filter are described as follows, but the general principals of the desirable filter structure can be understood from the foregoing and can be applied to filters used in any of the presently described tissue treatment systems and methods. The filter structure 1910 can include a filter 1915 and one or more rigid rings. In an exemplary embodiment, the filter 1915 can be formed of a single piece of material such as a mesh-like material that is sealed at a single seam. By using a single seam, the amount of mesh sealing that has to be performed during production can be reduced. In some embodiments, the filter structure 1910 can include an upper rigid ring 1922 and a lower rigid ring 1924. The upper rigid ring 1922 can include a sealing surface 1924 and a ridge 1925. In various embodiments, the sealing surface 1924 can be flat to allow for heat sealing or ultrasonic welding of the filter 1915 to the sealing surface 1924. The lower rigid ring 1924 can include a flat surface to facilitate heat sealing or ultrasonic welding of the filter 1915 to the lower rigid ring 1924. The rigid rings can be formed of plastic or any other suitable material including, but not limited to, metals or glass. In some embodiments, the filter 1915 can include a synthetic or natural mesh-like material. The filter 1915 can be a mesh wall that divides a first chamber from a second chamber. In some embodiments, the upper rigid ring 1922 can be a portion of a frame that surrounds the upper border of the filter 1915 such as a mesh.

FIG. 18B illustrates placement of the filter structure of FIG. 18A in a tissue treatment system according to various embodiments of the present disclosure. In some embodiments, the tissue treatment system can include an exoskeleton 1950. In an exemplary embodiment, the ridge 1925 on the upper rigid ring 1922 can engage with a shelf feature 1952 in the exoskeleton 1950. The engagement of the upper rigid ring 1922 and exoskeleton 1950 can include a sealing or press-fit step to let an assembler or practitioner know that the elements are engaged. In some embodiments, the lower rigid ring 1924 can be bonded or heat sealed to the exoskeleton 1950 to fix the mesh filter 1910 in place or to prevent leakage of tissue or fluids from within the mesh filter.

While the present invention has been described herein in conjunction with preferred embodiments, a person of ordinary skill in the art can effect changes, substitutions or equivalents to the systems and methods described herein, which are intended to fall within the appended claims and any equivalents thereof.

The invention claimed is:

1. A tissue treatment system, comprising:
a container, including:
an exterior wall surrounding an interior volume for holding tissue; and
a filter structure for processing tissue; and
a flow management device, including:
a first plate having a plurality of first openings passing therethrough;
a second plate having a plurality of second openings passing therethrough; and
a third plate having one or more third openings passing therethrough;
wherein the first plate, second plate, and third plate are operably connected and wherein setting the third plate in a first position places a first subset of the plurality of first openings in fluid communication with a first subset of the plurality of second opening, setting the third plate in a second position places a second subset of the plurality of first openings in fluid communication with a second subset of the plurality of second openings, and setting the third plate to a third position places a third subset of the plurality of first openings in fluid communication with a third subset of the plurality of second openings.

2. The tissue treatment system of claim 1, further comprising a rotatable connection to operably connect the first plate, the second plate, and the third plate.

3. The tissue treatment system of claim 1, further comprising a plurality of seals to prevent material from passing between the first plate and the third plate or the second plate and the third plate.

4. The tissue treatment system of claim 3, wherein at least one of the first plate, the second plate, and the third plate includes a plurality of recessed portions, and
wherein setting the first plate in a fourth position places the plurality of seals into the plurality of recessed portions and wherein none of the plurality of first openings is in fluid communication with a second opening.

5. The tissue treatment system of claim 1, further comprising at least one mixing blade to facilitate tissue washing or treatment.

6. The tissue treatment system of claim 1, wherein the first, second, and third positions of the third plate are configured to correspond to process steps in a tissue washing or processing procedure.

7. The tissue treatment system of claim 6, wherein the first position of the third plate are configured to correspond to a tissue aspiration step of the tissue washing or processing procedure.

8. The tissue treatment system of claim 6, wherein the second position of the third plate are configured to correspond to a tissue washing step of the tissue washing or processing procedure.

9. The tissue treatment system of claim 6, wherein the third position of the third plate are configured to correspond to a step of the tissue washing or processing procedure wherein tissue is transferred out of the container.

10. The tissue treatment system of claim 1, further comprising a transfer port in fluid communication with the interior volume.

11. The tissue treatment system of claim 1, further comprising a plurality of ports, each port in fluid communication with one of the plurality of first openings.

12. The tissue treatment system of claim 1, wherein the tissue treatment system is medically sterile.

13. The tissue treatment system of claim 1, wherein the container includes a first chamber and a second chamber divided by a dividing wall.

14. The tissue treatment system of claim 13, wherein the dividing wall is defined at least in part by the filter structure.

15. The tissue treatment system of claim 1, wherein the filter structure comprises a mesh wall and a frame supporting the mesh wall.

16. The tissue treatment system of claim 15, wherein the frame comprises a rigid material.

17. The tissue treatment system of claim 15, wherein the frame comprises a rigid material surrounding an upper border of the mesh wall.

18. The tissue treatment system of claim 15, wherein the frame comprises a rigid material surrounding an upper border of the mesh wall and extending along at least a portion of a side wall of the mesh wall to a bottom portion of the mesh wall.

19. The tissue treatment system of claim 15, wherein the frame comprises a rigid material surrounding an upper border of the mesh wall and having multiple extensions along at least a portion of a side wall of the mesh wall to a bottom portion of the mesh wall.

20. The tissue treatment system of claim 1, further comprising a transfer port at a bottom portion of the container.

21. The tissue treatment system of claim 20, wherein the transfer port is capable of fluid communication with a space inside the filter structure.

22. The tissue treatment system of claim 21, wherein the filter structure comprises a mesh wall and a frame supporting the mesh wall.

23. The tissue treatment system of claim 22, wherein the frame comprises a rigid material.

24. The tissue treatment system of claim 22, wherein the frame comprises a rigid material surrounding an upper border of the mesh wall.

25. The tissue treatment system of claim 22, wherein the frame comprises a rigid material surrounding an upper border of the mesh wall and extending along at least a portion of a side wall of the mesh wall to a bottom portion of the mesh wall, and wherein the frame is securely engaged with the transfer port.

26. The tissue treatment system of claim 22, wherein the frame comprises a rigid material surrounding an upper border of the mesh wall and having multiple extensions along at least a portion of a side wall of the mesh wall to a bottom portion of the mesh wall, and wherein the frame is securely engaged with the transfer port.

27. The tissue treatment system of claim 1, further comprising a wide base.

28. The tissue treatment system of claim 27, wherein the wide base has a widest dimension that is at least 10%, at least 20%, at least 30%, at least 40% greater than a widest dimension of a lowest portion of the container.

29. The tissue treatment system of claim 27, wherein the wide base has a widest dimension that is at least 10%, at least 20%, at least 30%, at least 40% greater than a widest dimension of a top of the tissue treatment system.

* * * * *